United States Patent
Ostrowski et al.

(10) Patent No.: US 10,527,633 B2
(45) Date of Patent: Jan. 7, 2020

(54) COMPOSITION COMPRISING PROSTACYCLIN ANDOR ANALOGUES THEREOF FOR TREATMENT OF ACUTE CRITICALLY ILL PATIENTS

(71) Applicant: Endothel Pharma ApS, Copenhagen K (DK)

(72) Inventors: Sisse Rye Ostrowski, Gentofte (DK); Pär Ingemar Johansson, Dösjebro (SE)

(73) Assignee: ENDOTHEL PHARMA APS, Copenhagen K (DK)

(*) Notice: Subject to any disclaimer, the term of this patent is extended or adjusted under 35 U.S.C. 154(b) by 3 days.

(21) Appl. No.: 15/562,259

(22) PCT Filed: Mar. 22, 2016

(86) PCT No.: PCT/EP2016/056236
§ 371 (c)(1),
(2) Date: Sep. 27, 2017

(87) PCT Pub. No.: WO2016/156107
PCT Pub. Date: Oct. 6, 2016

(65) Prior Publication Data
US 2018/0088131 A1    Mar. 29, 2018
US 2018/0246123 A9    Aug. 30, 2018

(30) Foreign Application Priority Data
Mar. 29, 2015  (DK) .................... 2015 00197
Jun. 15, 2015  (DK) .................... 2015 00342

(51) Int. Cl.
| | | |
|---|---|---|
| G01N 33/68 | (2006.01) | |
| G01N 33/58 | (2006.01) | |
| A61K 45/06 | (2006.01) | |
| A61K 31/5585 | (2006.01) | |

(52) U.S. Cl.
CPC ..... *G01N 33/6893* (2013.01); *A61K 31/5585* (2013.01); *A61K 45/06* (2013.01); *G01N 33/58* (2013.01); *G01N 33/68* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 2010/0204254 A1* | 8/2010 | Hauer-Jensen | A61K 31/22 514/275 |
| 2015/0079613 A1* | 3/2015 | McKnight | C07K 16/18 435/7.92 |

FOREIGN PATENT DOCUMENTS

| | | |
|---|---|---|
| WO | 2010/075861 A2 | 7/2010 |
| WO | 2011/134478 A2 | 11/2011 |
| WO | 2012/041334 A1 | 4/2012 |
| WO | 2012/143012 A1 | 10/2012 |
| WO | 2013/143548 A1 | 10/2013 |
| WO | WO-2013143548 A1 * | 10/2013 ........... A61K 31/519 |
| WO | 2015/074663 A1 | 5/2015 |

OTHER PUBLICATIONS

Zhang et al. (Am J. Clin Pathol. 2007 vol. 128, p. 287-292) (Year: 2007).*
Artenstein, Andrew W., et al., "Sepsis and Scientific Revolutions", Special Article, Critical Care Medicine, www.ccmjournal.org, vol. 41, No. 12, Dec. 2013, pp. 2770-2772.
Bärthel, Erik, et al."Impact of stable PGI2 analog iloprost on early graft viability after liver transplantation: a pilot study", Clinical Transplantation, Impact of iloprost after liver transplantation, 2012: 26, pp. E38-E47.
Beirne, Chris, et al., "Six Years' Experience with Prostaglandin I2 Infusion in Elective Open Repair of Abdominal Aortic Aneurysm: A Parallel Group Observational Study in a Tertiary Referral Vascular Center", Elsevier, PGI2 infusion in elective open AAA repair, vol. 22, No. 06, Nov. 2008, pp. 750-755.
Bihari, David, et al. "The Effects of Vasodilation With Prostacyclin on Oxygen Delivery and Uptake in Critically Ill Patients", The New England Journal of Medicine, vol. 317, No. 07, Aug. 13, 1987, pp. 397-403.
Boehme, Michael, W. J., et al., "Decrease in Circulating Endothelial Cell Adhesion Molecule and Thrombomodulin Levels During Oral Iloprost Treatment in Rheumatoid Arthritis Patients: Preliminary Results", Original Article, Rheumatology International, Feb. 2006, vol. 26, Issue 4, pp. 340-347.
Davies, Mark G., et al. "The Vascular Endothelium", A New Horizon, Review Article, Annals of Surgery, vol. 218, No. 05, Nov. 1993, pp. 593-609.
De Donato, G., et al., "Acute Limb Ischemia in Elderly Patients: Can Iloprost be Useful as an Adjuvant to Surgery? Results from the ILAILL Study", Eur J Vasc Endovasc Surg Aug. 2007, vol. 46, Issue 2, pp. 397-398.
De Donato, Gaetano, et al., "The ILAILL Study: Iloprost as Adjuvant to Surgery for Acute Ischemia of Lower Limbs, a Randomized, Placebo-Controlled, Double-Blind Study by the Italian Society for Vascular and Endovascular Surgery", Annals of Surgery, Randomized, Controlled Trials, vol. 244, No. 2, Aug. 2006, pp. 185-193.
Grande, P. O., et al., "Low-Dose Prostacyclin in Treatment of Severe Brain Trauma Evaluated With Microdialysis and Jugular Bulb Oxygen Measurements", Case Report, Acta Anaesthesiologica Scandinavica, vol. 44, No. 07, Aug. 2000, pp. 886-894.
Holmvang, Lene, et al., "A Single Center, Open, Randomized Study Investigating the Clinical Safety and the Endothelial Modulating Effects of a Prostacyclin Analog in Combination With Eptifibatide in Patients Having Undergone Primary Percutaneous Coronary Intervention (PCI) for St-Segment Elevation Myocardial Infarction", Prostaglandins and Other Lipid Mediators, Elsevier, vol. 99, No. 3-4, Dec. 2012, pp. 87-95.

(Continued)

*Primary Examiner* — Changhwa J Cheu
(74) *Attorney, Agent, or Firm* — Nordic Patent Service

(57) ABSTRACT

Use of prostacyclin or an analogue thereof for treatment of a new medical indication in acute critically ill patients, in particular acute critically ill patients with systemic endothelial damage, a biomarker for identifying individuals that have a new medical indication, and a method for identifying a new medical indication.

21 Claims, 18 Drawing Sheets

(56) References Cited

OTHER PUBLICATIONS

Johansson, Pär, et al., "A High Admission Syndecan-1 Level, a Marker of Endothetial Glycocalyx Degradation, Is Associated With Inflammation, Protein C Depletion, Fibrinolysis, and Increased Mortality in Trauma Patients", Journal Article, Randomized Controlled Trial, Research Support, Annals of surgery, Aug. 2011, vol. 254, pp. 194-200.
Johansson, P. I., et al., "Acute Coagulopathy of Trauma: Balancing Progressive Catecholamine Induced Endothelial Activation and Damage by Fluid Phase Anticoagulation", Elsevier, Medical Hypotheses, vol. 75, Issue 6, Dec. 2010, pp. 564-567.
Johansson, Pär, et al., "High Circulating Adrenaline Levels at Admission Predict Increased Mortality After Trauma", The journal of trauma and acute care surgery, Journal Article, Research Support, XP-002762327, Feb. 2012, vol. 72, pp. 428-436.
Johansson, P. I., et al., "High sCD4OL Levels Early After Trauma Are Associated With Enhanced Shock, Sympathoadrenal Activation, Tissue and Endothelial Damage, Coagulopathy and Mortality", Journal Thrombosis and Haemostasis, vol. 10, No. 02, Feb. 2012, pp. 207-216.
Kiefer, Peter, et al., "Hepato-Splanchnic Metabolic Effects of the Stable Prostacyclin Analogue Iloprost in Patients With Septic Shock", Original, Intensive Care Med., vol. 27, No. 7, Jul. 2001, pp. 1179-1186.
Lehmann, Christian, et al., "Effects of the Stable Prostacyclin Analogue Iloprost on the Plasma Disappearance Rate of Indocyanine Green in Human Septic Shock", Brief Report, Intensive Care Medicine, vol. 26, Issue 10, Oct. 2000, pp. 1557-1560.
Marshall, John C., "Why have clinical trials in sepsis failed?", Special issue: Sepsis, Opinion, Trends in Molecular Medicine, CellPress, vol. 20, No. 4, Apr. 2014, pp. 195-203.
Moncada, S., "An Enzyme Isolated From Arteries Transforms Prostaglandin Endoperoxides to an Unstable Substance That Inhibits Platelet Aggregation", Nature, vol. 263, Oct. 21, 1976, pp. 663-665.
Morgera, Stanislao, et al., "Low-Dose Prostacyclin Preserves Renal Function in High-Risk Patients After Coronary Bypass Surgery", Crit. Care Med. vol. 30, No. 01, 2002, pp. 107-112.
Naredi, S., et al., "An Outcome Study of Severe Traumatic Head Injury Using the "Lund Therapy" With Low-Dose Prostacyclin", Acta Anaesthesiologica Scandinavica, vol. 45, Issue 4, Apr. 2001, pp. 402-406.
Neumann, U.P., et al., "Reduction of Reperfusion Injury With Prostacyclin I2 After Liver Transplantation", Elsevier, Transplantation Proceedings, vol. 31, Issues 1-2, Feb.-Mar. 1999, pp. 1029-1030.
O'Grady, J., et al., "Effects of Intravenous Infusion of Prostacyclin (PGI2) in Man", Prostaglandins, vol. 19, No. 2, Feb. 1980, pp. 319-332.
Opal, S. M., et al., "Endothelial barrier dysfunction in septic shock", Journal of Internal Medicine, Review, vol. 277, Issue 3, Mar. 2015, pp. 277-293.
Radermacher P., et al., "The Effects of Prostacyclin on Gastric Intramucosal pH in Patients With Septic Shock", Original, Intensive Care Medicine, vol. 21, Issue 5, May 1995, pp. 414-421.
Scheeren, T., et al., "Prostacyclin (PGI2): New aspects of an old substance in the treatment of critically ill patients", Review, Intensive Care Med, XP-002594947, 1997, vol. 23, pp. 146-158.
Simmons, Jeff, et al., "The Coagulopathy of Acute Sepsis", Review, Current Opinion Anesthesiol, Apr. 2015, vol. 28, No. 02, Apr. 2015, pp. 227-236.
Windeløv, Nis A., et al., "Transfusion Requirements and Clinical Outcome in Intensive Care Patients Receiving Continuous Renal Replacement Therapy: comparison of prostacyclin vs. heparin prefilter administration", Original Article, Transfusions and clinical outcome in CRRT with PGI2, Blood Coagulation and Fibrinolysis., vol. 21, No. 5, Jul. 2010, pp. 414-419.
Zardi, Enrico Maria, et al., "Endothelial Dysfunction and Activation as an Expression of Disease: Role of Prostacyclin Analogs", International Immunopharmacology, Elsevier, vol. 5, Issue 3, Mar. 2005, pp. 437-459.
Zardi, Enrico Maria, et al., "Prostacyclin in sepsis: A systematic review", Prostaglandins & other Lipid Mediators, vol. 83, Issues 1-2, Feb. 2007, pp. 1-24.
Johansson, Pär, et al.,"The Effect of intraoperative and 6-h postoperative intravenous administration of low dose prostacyclin on the endothelium, hemostasis, and hemodynamics in patients undergoing a pancreaticoduodenoctemy: a randomized-controlled pilot study", Original Article, European Journal of Gastroenterololy and Hepatology, Apr. 2017, vol. 29, No. 4, pp. 400-406.
International Search Report of the European Patent Office, received for Application No. PCT/EP2016/056236, dated Oct. 21, 2016, 8 pages.

\* cited by examiner

| Syndecan-1 (ng/ml) | Sensitivity | 1-specificity |
|---|---|---|
| 25 ng/ml | 0.647 | 0.530 |
| 30 ng/ml | 0.595 | 0.475 |
| 35 ng/ml | 0.586 | 0.385 |
| 40 ng/ml | 0.569 | 0.354 |
| 50 ng/ml | 0.474 | 0.281 |
| 60 ng/ml | 0.431 | 0.236 |
| 70 ng/ml | 0.379 | 0.216 |

Fig. 23   Table 9

| Adrenaline (pg/ml) | Sensitivity | 1-specificity |
|---|---|---|
| 150 ng/ml | 0.721 | 0.565 |
| 175 ng/ml | 0.703 | 0.520 |
| 200 ng/ml | 0.667 | 0.480 |
| 225 pg/ml | 0.658 | 0.435 |
| 250 ng/ml | 0.622 | 0.410 |
| 300 ng/ml | 0.532 | 0.335 |
| 400 ng/ml | 0.441 | 0.249 |

Fig. 24   Table 10

|  | Prostacyclin treated | Heparin treated |
|---|---|---|
| Patients | n=24 | n=70 |
| ICU admission | | |
| APACHE II score | 26 | 28 |
| During ICU stay | | |
| Septic shock | 88% (n=21) | 67% (n=47) |
| DIC | 58% (n=14) | 26% (n=18) |
| Severe thrombocytopenia | 71% (n=17) | 44% (n=31) |
| Platelet count at start of CRRT ($*10^9/1$) | 39 | 93 |
| Platelet count at the end of CRRT ($*10^9/1$) | 53 | 76 |
| Platelet count difference from before to after CRRT ($*10^9/1$) | +14 | -17 |
| Outcome | | |
| 30-day mortality | 21% | 39% |

Fig. 12    Table 1

| Disease | n | Gender | All | Death (28d) | %Mortality (28d) | Survivors (28d) |
|---|---|---|---|---|---|---|
| Trauma | 635 | All | 4.65 | 5.27 | 18% | 4.47 |
| | | Male | 4.68 | 5.30 | | 4.60 |
| | | Female | 4.38 | 5.14 | | 3.93 |
| Myocardial infarction | 571 | All | 2.17 | 3.23 | 6% | 2.09 |
| | | Male | 2.06 | 2.54 | | 2.03 |
| | | Female | 2.56 | 3.86 | | 2.43 |
| Cardiac arrest | 163 | All | 6.97 | 7.78 | 33% | 6.56 |
| | | Male | 7.33 | 8.12 | | 6.73 |
| | | Female | 5.21 | 6.08 | | 5.02 |
| Sepsis/severe sepsis/septic shock | 749 | All | 9.22 | 10.96 | 35% | 8.52 |
| | | Male | 9.57 | 12.57 | | 8.87 |
| | | Female | 8.35 | 9.91 | | 7.82 |
| All patients | 2,118 | All | 4.93 | 8.31 | 22% | 4.20 |
| | | Male | 4.87 | 8.52 | | 4.04 |
| | | Female | 5.05 | 7.65 | | 4.42 |

Fig. 13   Table 2

| Thrombomodulin level cut-off in plasma | Sensitivity (true-positive rate) | 1-Specificity (false-positive rate) | Youden's Index (statistic parameter that captures the performance of a diagnostic test) |
|---|---|---|---|
| 2.5 ng/ml | 0.907 | 0.666 | 0.241 |
| 3.0 ng/ml | 0.885 | 0.568 | 0.317 |
| 3.5 ng/ml | 0.848 | 0.491 | 0.357 |
| 4.0 ng/ml* | 0.781 | 0.407 | 0.375 |
| 4.5 ng/ml | 0.719 | 0.355 | 0.363 |
| 5.0 ng/ml | 0.667 | 0.304 | 0.363 |
| 5.5 ng/ml | 0.581 | 0.240 | 0.342 |

*The level chosen herein based on Youden Index

Fig. 14  Table 3

| sTM level | Severely injured patients Admission | Moderately injured patients Admission | 24h | 72h |
|---|---|---|---|---|
| > 2.5 ng/ml | 84.9% | 45.2% | 68.5% | 80.0% |
| > 3.0 ng/ml | 79.3% | 31.9% | 48.3% | 67.3% |
| > 3.5 ng/ml | 71.2% | 25.2% | 42.7% | 52.7% |
| > 4.0 ng/ml | 60.8% | 16.3% | 29.2% | 45.5% |
| > 4.5 ng/ml | 51.9% | 10.0% | 21.3% | 32.7% |
| > 5.0 ng/ml | 44.2% | 6.3% | 15.7% | 21.8% |
| > 5.5 ng/ml | 33.8% | 3.7% | 12.4% | 18.2% |

Table 4a

Fig. 15

| Time-interval | Absolute change | Proportional change |
|---|---|---|
| Admission to 24h | +0.59 ng/ml | +23% |
| Admission to 72h | +0.72 ng/ml | +34% |
| 24h to 72h | +0.31 ng/ml | +12% |

Table 4b

Fig. 16

| sTM level | Admission | 24h | 48h | 72h |
|---|---|---|---|---|
| > 2.5 ng/ml | 98.1% | 100.0% | 100.0% | 100.0% |
| > 3.0 ng/ml | 98.1% | 98.7% | 99.3% | 98.6% |
| > 3.5 ng/ml | 96.3% | 97.4% | 98.7% | 93.9% |
| > 4.0 ng/ml | 92.0% | 93.5% | 96.0% | 90.5% |
| > 4.5 ng/ml | 88.9% | 90.3% | 94.0% | 87.8% |
| > 5.0 ng/ml | 84.6% | 83.8% | 90.1% | 83.1% |
| > 5.5 ng/ml | 71.6% | 76.6% | 82.8% | 75.0% |

Fig. 17  Table 5a

| Time-interval | Survivors | | non-survivors | |
|---|---|---|---|---|
| | Absolute change | Proportional change | Absolute change | Proportional change |
| Admission to 24h | -0.03 | 0% | +0.67 | +16% |
| Admission to 48h | +1.04 | +19% | +1.31 | +28% |
| Admission to 72h | +0.87 | +10% | +0.4 | +9% |

Fig. 18  Table 5b

| sTM level | CPC 3-5 [(AUC (95%CI), p-value] | mRS 4-6 [(AUC (95%CI), p-value] |
|---|---|---|
| Admission | 0.663 (0.577-0.748), p<0.001 | 0.651 (0.564-0.738), p<0.001 |
| 24h | 0.628 (0.533-0.723), p=0.009 | 0.632 (0.538-0.725), p=0.008 |
| 48h | 0.619 (0.524-0.714), p=0.016 | 0.629 (0.535-0.722), p=0.010 |
| 72h | 0.601 (0.500-0.703), p=0.044 | 0.609 (0.508-0.709), p=0.032 |

Fig. 19  Table 5c

| sTM level   | Admission |
|-------------|-----------|
| > 2.5 ng/ml | 41.3%     |
| > 3.0 ng/ml | 26.3%     |
| > 3.5 ng/ml | 17.3%     |
| > 4.0 ng/ml | 10.2% |
| > 4.5 ng/ml | 6.5%      |
| > 5.0 ng/ml | 3.5%      |
| > 5.5 ng/ml | 1.9%      |

Fig. 20  Table 6

| sTM level   | Admission  |
|-------------|------------|
| > 2.5 ng/ml | 90-94%     |
| > 3.0 ng/ml | 90-93%     |
| > 3.5 ng/ml | 87-91%     |
| > 4.0 ng/ml | 84-90% |
| > 4.5 ng/ml | 80-87%     |
| > 5.0 ng/ml | 77-84%     |
| > 5.5 ng/ml | 73-81%     |

Fig. 21  Table 7

Table 1. Demography data and thrombomodulin levels in plasma and whole blood from 10 healthy volunteers.

| | | | | Plasma diluted 1:2 | | | Whole blood undiluted | | | | | Whole blood diluted 1:2 | | | | | Whole blood diluted 1:4 | | | | |
|---|---|---|---|---|---|---|---|---|---|---|---|---|---|---|---|---|---|---|---|---|---|
| ID | Sex | Age | Hct | Mean conc | SD | CV% | Mean conc | SD | CV% | Conc. hct corrected | Recovery | Mean conc | SD | CV% | Conc. hct corrected | Recovery | Mean conc | SD | CV% | Conc. hct corrected | Recovery |
| 1 | F | 57 | 0.42 | 1.56 | 0.02 | 1.4% | 0.63 | 0.04 | 6.0% | 1.08 | 69.4% | 1.15 | 0.06 | 5.1% | 1.97 | 126.8% | 0.54 | 0.03 | 4.7% | 0.93 | 59.6% |
| 2 | F | 37 | 0.42 | 2.07 | 0.11 | 5.1% | 0.94 | 0.14 | 15.4% | 1.62 | 78.1% | 1.63 | 0.04 | 2.6% | 2.81 | 135.9% | 1.72 | 0.27 | 15.6% | 2.96 | 143.1% |
| 3 | M | 55 | 0.47 | 2.32 | 0.16 | 6.8% | 0.86 | 0.08 | 9.2% | 1.63 | 70.1% | 1.52 | 0.15 | 9.9% | 2.86 | 123.3% | 1.54 | 0.26 | 16.9% | 2.90 | 125.0% |
| 4 | M | 60 | 0.47 | 1.90 | 0.21 | 11.2% | 0.78 | 0.01 | 1.4% | 1.47 | 77.3% | 1.13 | 0.06 | 4.9% | 2.13 | 112.1% | 0.93 | 0.14 | 14.8% | 1.76 | 92.7% |
| 5 | F | 58 | 0.42 | 1.80 | 0.01 | 0.4% | 0.66 | 0.06 | 9.6% | 1.13 | 62.7% | 1.03 | 0.11 | 10.2% | 1.77 | 98.3% | 0.76 | 0.15 | 19.8% | 1.31 | 72.5% |
| 6 | F | 32 | 0.42 | 2.15 | 0.07 | 3.3% | 0.82 | 0.04 | 4.3% | 1.42 | 65.9% | 1.36 | 0.10 | 7.6% | 2.34 | 109.1% | 1.04 | 0.26 | 24.4% | 1.80 | 83.8% |
| 7 | F | 37 | 0.42 | 1.36 | 0.16 | 12.0% | 0.62 | 0.05 | 7.9% | 1.07 | 78.6% | 0.66 | 0.11 | 16.5% | 1.14 | 84.0% | 0.30 | | | 0.52 | 38.6% |
| 8 | F | 36 | 0.42 | 2.27 | 0.10 | 4.5% | 0.99 | 0.01 | 1.1% | 1.70 | 74.9% | 1.55 | 0.06 | 3.6% | 2.68 | 117.9% | 1.44 | 0.20 | 13.6% | 2.48 | 109.2% |
| 9 | F | 47 | 0.42 | 1.47 | 0.33 | 22.1% | 0.55 | 0.15 | 27.3% | 0.94 | 64.1% | 0.81 | 0.19 | 23.3% | 1.39 | 94.8% | 0.51 | 0.29 | 57.1% | 0.88 | 59.7% |
| 10 | F | 52 | 0.42 | 2.32 | 0.06 | 2.4% | 1.00 | 0.06 | 6.2% | 1.72 | 74.3% | 1.43 | 0.28 | 19.8% | 2.47 | 106.4% | 1.58 | 0.36 | 22.9% | 2.73 | 117.7% |
| Mean | | | | 1.92 | 0.12 | 6.9% | 0.78 | 0.06 | 8.8% | 1.38 | 71.5% | 1.23 | 0.12 | 10.4% | 2.16 | 110.9% | 1.04 | 0.22 | 21.1% | 1.83 | 90.2% |
| SD | | | | 0.36 | | | 0.16 | | | 0.30 | 5.9% | 0.33 | | | 0.59 | 15.8% | 0.51 | | | 0.90 | 33.4% |

Hct, hematocrit. Mean concentration of a duplicate sample in ng/ml. SD, standard deviation. CV%, coefficient of variation (SD/mean*100). Concentration hct corrected, = mean concentration / (1-hct). Recovery, proportion of thrombomodulin detected in whole blood relative to the amount detected in plasma = (concentration in whole blood / concentration in plasma) *100.

Fig. 22  Table 8

COMPOSITION COMPRISING PROSTACYCLIN ANDOR ANALOGUES THEREOF FOR TREATMENT OF ACUTE CRITICALLY ILL PATIENTS

FIELD

The aspects of the disclosed embodiments relate to novel uses of prostacyclin and analogues thereof for treatment of patients suffering from acute critical illness. The aspects of the disclosed embodiments also relate to a method of identifying patients with a newly identified disease entity in order to initiate treatment earliest possible, pre-hospital as well as in-hospital, after the injurious hit.

BACKGROUND

Acute critical illness such as trauma, sepsis and resuscitated cardiac arrest affects millions of people worldwide annually with a projected 40% increase in global deaths due to injuries in the period 2002 to 2030. Approximately one quarter of acute critically ill patients develop severe hemostatic aberrations resulting in impaired clotting ability (coagulopathy); such acute critically ill patients with coagulopathy having 3-4 times higher mortality rates compared to their non-coagulopathic counterparts (40-50% vs. 10-15%). Importantly, besides early mortality related to exsanguination, acute critically ill patients with coagulopathy have a several-fold increased risk of developing and dying from multiple organ failure in the days and weeks that follow the injurious hit. Regrettably, the outcome for acute critically ill patients with coagulopathy has remained unaltered since the 1970ies, despite a general improvement in intensive care capabilities, pointing towards a lack of identification of the pathophysiologic mechanism(s) responsible for the poor outcome [Artenstein et al 2013; Marshall 2014]. Currently, no drugs/pharmacological agents or therapeutic interventions are registered to specifically treat coagulopathy in acute critically ill patients.

Microcirculatory failure is a hallmark of acute critical illness that is caused by numerous injurious hits to the vascular system, including the endothelium, i.e. the single layer of cells that lines the interior of all blood vessels in the body. Although there is emerging consensus that endothelial damage is a critical contributing factor to the development of organ failure and poor outcome in acute critically ill patients [Opal and van der Poll 2015], no drugs or therapies are currently registered to specifically treat endothelial damage in acute critically ill patients. There is thus an urgent unmet need for diagnostic tests and therapeutic interventions capable of reversing and treating the deleterious changes observed in the vascular system, including the endothelium, in acute critically ill patients [Marshall 2014; Simmons and Pittet 2015].

The Endothelium

The endothelium is the collective thin layer of cells (endothelial cells) that lines the interior of all blood and lymphatic vessels throughout the body. It is one of the largest "organs" in the human body having a total weight of approximately 1 kg and covering a total surface area of approximately 4-7,000 $m^2$. The luminal surface of the endothelial cells is covered by a 0.2-1.0 µm thick negatively charged carbohydrate-rich surface layer, the endothelial glycocalyx, that also represents a large structure in the vascular system by containing a fixed non-circulating plasma volume of approximately 1 liter in adults, corresponding to one third of the intravascular plasma volume.

The glycocalyx provides the endothelium with an anti-adhesive and anticoagulant surface that protects the endothelial cells and maintains vascular barrier function. The glycocalyx is a mesh-like structure comprising proteoglycan and glycoprotein backbone molecules that bind and incorporate various soluble molecules derived from the plasma and endothelium, with the highest amounts of plasma derived constituents towards the luminal surface.

The endothelium is critically involved in maintaining the delicate homeostasis between the circulating blood and all vital organs. By traversing each and every organ in the body, the endothelium is pivotal for maintaining homeostasis between the circulating blood and all vital organs and cells of the body and, hence, damage to the endothelium is a key factor of the observed poor outcome in acute critically ill patients. The endothelium controls vasomotor balance, vascular integrity, blood cell adhesion and trafficking, immune surveillance, inflammation and angiogenesis, and it is instrumental for balancing hemostasis through its release, expression and support of systems and elements that either promote or inhibit hemostasis.

In a healthy state, the endothelium is anticoagulated by constituents of the glycocalyx and the endothelial cells themselves. Upon endothelial damage, these constituents are released to the flowing blood while retaining their anticoagulant effects, thereby contributing to coagulopathy of acute critical illness. At the same time, the damaged endothelium becomes prothrombotic and triggers formation of microvascular thrombosis resulting in impaired oxygen delivery to tissues, organ failure and ultimately death [Johansson and Ostrowski 2010]. Furthermore, endothelial damage disrupts the inter-cellular tight junctions responsible for maintaining endothelial barrier function between the flowing blood and the tissues. This results in capillary leakage, which further drives hypotension and oxygen deprivation and thereby contribute directly to multiple organ failure and death [Opal and van der Poll 2015].

Until now, most research on acute critically ill patients with coagulopathy has been limited to studying circulating factors of single pathways such as the coagulation-, complement- and inflammatory systems readily measured in the plasma of patients. However, recognizing that the circulating plasma is only one part of the complex vascular system, which includes blood cells (platelets, leukocytes, red blood cells), microparticles and all the vessels that contain the blood, the inventors hypothesized that the observed plasma aberrations reflect a universal, evolutionary developed response to acute critical illness that is associated with concurrent changes in the vascular endothelium and circulating blood cells [Johansson and Ostrowski 2010].

Prostacyclin

Prostacyclin is a naturally occurring prostaglandin released by healthy endothelial cells. In humans, prostacyclin generation by the vascular endothelium is approximately 0.08-0.10 ng/kg/min with a maximal concentration of 3.4 pg/1 in the circulation [Davies and Hagen 1993]. Prostacyclin performs its function through a paracrine signaling cascade that involves G protein-coupled receptors (GPCR) on nearby endothelial cells and platelets.

The two main pharmacologic actions of prostacyclin and its analogues are vasodilation and inhibition of platelet aggregation, which is reflected by the current medical indications for prostacyclin analogs [including but not limited to Iloprost, Epoprostenol, Epoprostenol Sodium, treprostenil sodium, selexipag, Beraprost, etc. administered either intravenously (i.v.), subcutaneously (s.c.) or oral (p.o.)]:

1) primary pulmonary hypertension (NYHA class III-IV patients)
2) secondary pulmonary hypertension (NYHA class III-IV patients with the scleroderma spectrum of disease who do not respond adequately to conventional therapy)
3) anticoagulation during hemodialysis or renal replacement therapy when heparin is contraindicated
4) peripheral arterial disease with imminent risk of amputation when surgical treatment and angioplasty is not possible
5) progressive thrombangitis obliterans (mb. Bürger) with critical limb ischemia when surgical treatment and angioplasty is not possible A study in human volunteers reported that prostacyclin at doses less than 8 ng/kg/min had no significant effect on systolic or diastolic blood pressure whereas a dose of 8 ng/kg/min reduced diastolic blood pressure. The study found no effect on systolic blood pressure in doses up to 16 ng/kg/min [O'Grady et al 1980]. However, several studies have reported that prostacyclin in doses from 5-10 ng/kg/min lowers systolic blood pressure dose-dependently in acute critically ill patients [Bihari et al 1987; Radermacher et al 1995].

In healthy volunteers, 1-4 ng/kg/min prostacyclin infusion did not influence blood pressure and in patients suffering from traumatic brain injury [Grande et al 2000; Naredi et al 2001], acute myocardial infarction treated by percutaneous coronary intervention (PCI) [Holmvang et al 2012], septic shock [Kiefer et al 2001; Lehmann et al 2000] or CABG surgery [Morgera et al 2002], 0.5-2 ng/kg/min prostacyclin infusion did not negatively influence blood pressure.

In conclusion it was found that prostacyclin dilates all vascular beds dose-dependently but the hemodynamic effects of low-dose prostacyclin infusion (up to 4 ng/kg/min) are negligible in healthy volunteers and in acute critically ill patients.

Inhibition of Platelet Aggregation

Prostacyclin inhibition of platelet aggregation is mediated through platelet expressed GPCR (IP), which upon prostacyclin binding signals adenylyl cyclase to produce cAMP, which activates PKA to decrease free intracellular calcium concentrations. The rise in cAMP directly inhibits platelet activation (secretion and aggregation) and counteracts increases in cytosolic calcium resulting from platelet activation by platelet agonists.

Historically, prostacyclin has been considered to be the most potent endogenous inhibitor of platelet aggregation in the human organism [Moncada et al 1976; O'Grady et al 1980]. However, as for the vasodilatory effect, the antiaggretory effect is highly dose-dependent [Moncada et al 1976; O'Grady et al 1980]. Of paramount importance for the suggested intervention, the inventors have investigated the anti-thrombotic potential of prostacyclin with functional whole blood hemostatic assays proven to correlate with clinical bleeding conditions and transfusion requirements (thrombelastography (TEG) and impedance aggregometry (Multiplate)) and surprisingly they discovered that low-dose prostacyclin infusion had no measurable anti-thrombotic effects.

In addition to the dose-dependent pharmacologic actions of prostacyclin (vasodilation and inhibition of platelet aggregation), there is emerging evidence that endogenously released prostacyclin has a paracrine cytoprotective function that is mimicked by prostacyclin analogs. This notion is considered important for the suggested intervention as acute critical illness disrupts normal prostacyclin release by endothelial cells leaving the patients with a malfunctioning systemically disrupted vascular endothelium.

Cytoprotection

The cytoprotective action of prostacyclin is mediated through prostacyclin IP receptors expressed on a broad range of cells including endothelial cells.

At the endothelial level, prostacyclin cytoprotection results in preservation and/or promotion of endothelial integrity and endothelial quiescence favoring an anticoagulant, antiadhesive, antiapoptotic and antiinflammatory phenotype of the endothelium. Prostacyclin directly promotes recruitment of endothelial progenitor cells, which enhances endothelial re-endothelilization of injured endothelium, inhibits endothelial apoptosis and prevents mitochondrial uncoupling of phosphorylation from oxidation in the respiratory chain in conditions with cellular stress, whereby mitochondrial structure and function is preserved and apoptosis reduced. Also, prostacyclin improves endothelial integrity and vascular barrier function by upregulating vascular endothelial (VE)-cadherin, which is responsible for maintaining tight junctions between endothelial cells. Finally, prostacyclin promotes endothelial quiescence by enhancing endothelial expression of other (besides prostacyclin) natural anticoagulant pathways which all, to some degree, exerts cytoprotive functions.

In addition to the direct action of prostacyclin on endothelial cells, the influence of prostacyclin on other cells and tissues indirectly protect the endothelium. Thus, prostacyclin induced vasodilation mediated through vascular smooth muscle relaxation protects the endothelium by ensuring microvascular perfusion and oxygen supply to (potentially hypoxic) cells and tissues. Also, prostacyclin stabilizes lysozomal and cell membranes in immunologic cells which reduces inflammation hereby preventing bystander activation and potential damage of the endothelium [Zardi et al 2005; Zardi et al 2007]. Finally, prostacyclin induced inhibition of platelet aggregation indirectly preserves endothelial quiescence as activated platelets promote endothelial activation.

In conclusion, prostacyclin exerts widespread cytoprotective actions that result in preservation and/or promotion of endothelial integrity and quiescence favoring an anticoagulant, antiadhesive, antiapoptotic and antiinflammatory phenotype of the endothelium thus counteracting the pathologic state of the endothelium in systemic endotheliopathic syndrome.

DEFINITIONS

The term "acute critical illness", is meant to include any condition rendering the patient in immediate need for intensive care therapy. The condition may be caused by any acute and extensive injurious hit to the body including but not limited to physical trauma, burn injury trauma, infection (hereunder sepsis, severe sepsis, septic shock), systemic inflammatory response syndrome (SIRS), acute myocardial infarction or other thromboembolic events.

The term "intensive care therapy", also term "organ supportive care" here, may include but is not limited to ventilation therapy (e.g. mechanical ventilation), hemodialysis, vasopressor therapy, fluid therapy, blood transfusion therapy with administration of red blood cell concentrates, fresh frozen plasma, platelet concentrates, whole blood or coagulation factor concentrates, systemic antibiotic and/or antiviral and/or antifungal and/or antiprotozoic therapy, parenteral nutrition, granulocyte infusion, T cell infusion, stem cell infusion, anticoagulant and/or antithrombotic therapy including low molecular weight heparins, administration of corticosteroids, tight glycemic control etc.

The term "trauma" as used herein means any shock or body wound produced by a sudden physical injury such as accident, injury or impact to living tissue caused by an extrinsic agent such as blast trauma, blunt trauma, penetrating trauma, trauma caused by chemical injury (spills, warfare or intoxication), radiation or burns.

The term "shock" is used in the conventional clinical meaning, i.e. shock is a medical emergency in which the organs and tissues of the body are not receiving an adequate flow of blood. This deprives the organs and tissues of oxygen (carried in the blood) and allows the build-up of waste products. Shock is caused by five major categories of problems: cardiogenic (meaning problems associated with the heart's functioning); hypovolemic/hemorrhagic (meaning that the total volume of blood available to circulate is low); neurogenic (caused by severe injury to the central nervous system), septic (caused by overwhelming infection, usually by bacteria) or anaphylactic/allergic (caused by systemic histamine release from immune cells and excessive vasodilation).

The term "treatment with prostacyclin or analogues thereof", as used in this application, means intravenous treatment of acute critically ill patients or continued critically ill patients with prostacyclin or analogues thereof.

The terms "treatment" and "treating" as used herein refer to the management and care of a patient for the purpose of combating an acute condition, disease or disorder. The term is intended to include the full spectrum of treatments for a given condition from which the patient is suffering, such as administration of prostacyclin or analogues thereof for the purpose of: ameliorating, alleviating or relieving symptoms or complications; delaying the progression of the condition, disease or disorder; curing or eliminating the condition, disease or disorder; and/or reducing the risk of or preventing the condition, disease or disorder, including preventing recurrence of the disease, wherein "preventing" or "prevention" is to be understood to refer to the management and care of a patient for the purpose of hindering the development of the condition, disease or disorder, and includes the administration of the pharmaceutical compositions to prevent the onset of symptoms or complications. The individual to be treated is a human being. An individual to be treated according to the present invention can be of various ages and can be both female and male.

The term "thrombomodulin" or TM or CD141 or BDCA-3, is an integral membrane protein expressed on the surface of endothelial cells serving as a cofactor for thrombin. It reduces blood coagulation by converting thrombin to an anticoagulant enzyme from a procoagulant enzyme. It is encoded by the THBD gene.

The term "soluble thrombomodulin" or "sTM" refers to a soluble form of thrombomodulin present in blood and other body fluids in human. A high circulating level of soluble thrombomodulin in the blood may either reflect increased shedding or release of thrombomodulin from the endothelium or reduced metabolism or excretion (the latter is typical finding in patients with chronic kidney disease). A low circulating level of thrombomodulin reflects that the shedding or release of thrombomodulin is low/normal.

The term "thrombomodulin level" used herein refers to the level of thrombomodulin in the circulating blood of a human, including the level in whole blood, plasma or serum. A given thrombomodulin level measured in plasma with the result ng/ml plasma, may not correspond to the thrombomodulin level measured in whole blood with the result ng/ml whole blood as the plasma fraction of whole blood is only approximately 55%.

The term "high thrombomodulin" (FIG. 7) refers to a plasma concentration of thrombomodulin above 4 ng/ml in a blood sample drawn from an acute critically ill patient earliest possible. With earliest possible means that the blood sample should be drawn minutes to hours after the injurious hit either pre-hospital, at hospital admission or upon occurrence of the acute critical illness in-hospital. Thrombomodulin reveals an area under the receiver operating characteristic (ROC) curve of 0.744 (0.712-0.776) in predicting 28-day mortality. The level 4 ng/ml reveals a sensitivity (true-positive rate) of 0.781 and a 1-specificity (false-positive rate) of 0.407 and the highest possible Youdens Index (a single statistic parameter that captures the performance of a diagnostic test).

Choosing a lower threshold level of thrombomodulin results in increased true-positive rate (sensitivity) and false-positive rate (1-specificity); whereas choosing a higher threshold level of thrombomodulin results in reduced true-positive rate (sensitivity) and false-positive rate (1-specificity) (Table 3). Both a lower or higher threshold level of thrombomodulin will thus result in a lower Youden Index and hence lower performance of the diagnostic test.

It should be noted that a thrombomodulin level of 4 ng/ml in plasma may not correspond to the thrombomodulin level measured in whole blood since the plasma fraction of whole blood is only approximately 55%.

The term "low thrombomodulin" (FIG. 7) refers to a plasma concentration of thrombomodulin below 4 ng/ml in a blood sample drawn from an acute critically ill patient earliest possible. With earliest possible means that the blood sample should be drawn minutes to hours after the injurious hit either pre-hospital, at hospital admission or upon occurrence of the acute critical illness in-hospital. A lower thrombomodulin level in an acute critically ill patient is associated with an increased change of a good clinical outcome.

The term "standard care" (FIG. 7) refers to but is not limited to the normal care and/or treatment a patient receives in the hospital such as ventilation therapy (e.g. mechanical ventilation), hemodialysis, vasopressor therapy, fluid therapy, blood transfusion therapy with administration of red blood cell concentrates, fresh frozen plasma, platelet concentrates, whole blood or coagulation factor concentrates, systemic antibiotic and/or antiviral and/or antifungal and/or antiprotozoic therapy, parenteral nutrition, granulocyte infusion, T cell infusion, stem cell infusion, anticoagulant and/or antithrombotic therapy including low molecular weight heparins, administration of corticosteroids, tight glycemic control etc.

The term "early treatment" (FIG. 7) refers herein to early as possible treatment with prostacyclin or analogues thereof optimally already pre-hospital or within minutes or hours after admission to the hospital or within minutes or hours upon the occurrence of an in-hospital injurious hit. The i.v. infusion with prostacyclin or analogues thereof in the dose should begin as early as possible after the thrombomodulin test results has become available i.e., within 30 min-6 hours after known test results, pre-hospital as well as in-hospital.

The term "lower T-level" (FIG. 7) refers to a lower-than-baseline level of thrombomodulin where baseline refers to the first initial time-point where thrombomodulin is measured. Thus, at all time-points post-baseline where thrombomodulin is measured, the decision to continue or cease prostacyclin treatment for the following 24 hours depends on the current thrombomodulin level as compared to the baseline thrombomodulin level. The therapy is thus personalized for the individual patient.

The term "improved CC" (FIG. 7) or "improved clinical condition" refers to an improvement in the clinical condition of the patient and/or a reduction in patient requirement for organ supportive care, which is either based on the attending doctors/medical staffs impression or on more objective criteria such as disease severity scores like, but not limited to, Sequential Organ Failure Assessment (SOFA) score. A reduction in requirement for organ supportive care could be but is not limited to reduced need for vasopressor treatment, reduced need for ventilator support and reduced need for oxygen, reduced need for dialysis etc.

The term "continue prostacyclin and standard care" (FIG. 7) means that the prostacyclin treatment should continue for another 24 hours in addition to stand care. This decision is based on the thrombomodulin level and the clinical condition of the patient.

The term "pre-hospital" refers to the phase before the patient reaches the hospital either at the scene of the accident or injurious hit (while the patients receives lifesaving emergency care treatment or is stabilized for transportation to the hospital) or during transportation to the hospital (by car, helicopter, plain, boat, train etc.). Pre-hospital treatment refers to any treatment being initiated before the patient reaches the hospital.

The term "individual" refers to a human subject.

The term "patient" refers to a human subject that is ill and/or requires medical treatment.

The term "personalized medicine" refers herein to an individualized treatment where patients with high thrombomodulin levels are treated with prostacyclin or analogues thereof whereas patients with low thrombomodulin levels (whom may look similar clinically to patients with high thrombomodulin levels) are not treated with prostacyclin or analogues thereof.

The term "prostacyclin" refers to the lipid molecule prostacyclin ($PGI_2$), which is a member of the eicosanoids family. The definition as used herein also includes prostacyclin analogs, prostacyclin variants or prostacyclin receptors agonists which have affinity for prostacyclin receptors and may be able to mediate functions similar to the functions mediated by prostacyclin i.e., the prostacyclin analogs or variants are functional equivalents of prostacyclin.

The terms "analogue" or "variant" are meant as any analogue or variant of a compound capable of treating a certain condition of the human body, particularly analogs and/or variants of prostacyclin which are functional equivalents of the compound.

The term "prostacyclin analogue", "prostacyclin variant" or "prostacyclin receptor agonist" have affinity for prostacyclin receptors and may be able to mediate functions similar to the functions mediated by prostacyclin i.e., the prostacyclin analogs, prostacyclin variants and prostacyclin receptor agonists are functional equivalents of prostacyclin. These compounds include but are not limited to Iloprost, Epoprostenol, Epoprostenol Sodium (flolan), Selexipag, Beraprost, Beraprost Sodium, Treprostinil, Treprostenil Sodium, Pegylated Treprostinil, Treprostinil Diethanolamine, 2-{4-[(5,6-diphenylpyrazin-2-yl)(isopropyl)amino]butoxy}-N-(methylsulfonyl) acetamide (long acting prostacyclin receptor agonist prodrug), {4-[(5,6-diphenylpyrazin-2-yl)(isopropyl)amino]butoxy}acetic acid, 8-[1,4,5-triphenyl-1H-imidazol-2-yl-oxy]octanoic acid (IP receptor agonist), carbacyclin (prostacyclin analog), isocarbacyclin (prostacyclin analog), cicaprost (prostacyclin analog), 7,8-dihydro-5-(2-(1-phenyl-1-pyrid-3-yl-methimi- noxy)-ethyl)-a-naphthyloxyacetic acid (IP receptor-specific non-prostanoid), 2-[3-[2-(4,5-diphenyl-2-oxazolyl)ethyl]phenoxy]acetic acid (non-prostanoid prostacyclin partial agonist), [3-[4-(4,5-diphenyl-2-oxazolyl)-5-oxazolyl]phenoxy]acetic acid (non-prostanoid prostacyclin partial agonist), 17[alpha], 20-dimethyl-[DELTA]6,6a-6a-carba PGI1 (non-prostanoid prostacyclin partial agonist), 15-deoxy-16[alpha]-hydroxy-16[beta],20-dimethyl-[DELTA]6,6a-6a-carba PGI1 (non-prostanoid prostacyclin partial agonist).

The terms "prostacyclin analogue", "prostacyclin variant" or "prostacyclin receptor agonist" refer to a drug that can initiate a physiologic or a pharmacologic response characteristic of prostacyclin. Prostacyclin analogs, prostacyclin variants and prostacyclin receptor agonists according to the present invention includes, but are not limited to, compounds that have affinity for the prostacyclin receptor and are capable of activating a prostacyclin receptor response in a manner similar to prostacyclin.

The term "protection" refers to reversal, reduction, ameliorating, alleviating or relieving degradation of the endothelium and its glyocalyx, the endothelium and/or glycocalyx themselves; delaying the progression of the endothelial cell damage, glycocalyx degradation; increasing endothelial cell rejuvenation and increasing the production of the glycocalyx and components of the glycocalyx, and/or reducing the risk of, or preventing the damage to endothelial cells and degradation of the glycocalyx.

The term "endothelial modulating effects" is intended to mean pharmacological treatment aiming at maintaining or bringing the endothelium into a quiescent inactivated, antiadhesive, anticoagulant and anti-inflammatory state hereby preserving, restoring or promoting vascular integrity and normal functional responsiveness of the endothelium.

The term "endothelial modulator" encompasses any agent or compound that influences the endothelium to either maintain or develop into a state which optimally preserves and ensures vascular integrity and normal functional responsiveness. In a state with maintained vascular integrity, the endothelium also exerts quiescent inactivated, antiadhesive, anticoagulant and anti-inflammatory properties.

The term "dose" as used herein means a dose sufficient to produce the desired effect in relation to the conditions for which it is administered, in particular an amount of a compound capable of modulating, protecting and/or treating the endothelium and hereby treat systemic endotheliopathic syndrome. Normally the dose should be capable of preventing or lessening the severity or spread of the condition or indication being treated. The exact dose will depend on the circumstances, such as the condition being treated, the administration schedule, the half-life of the compound capable of modulating, protecting and/or treating the endothelium and the general health of the subject.

The term "thrombelastography" or "TEG" refers to a commercially available viscoelastic whole blood hemostasis assay employing citrated or non-anticoagulated blood. The TEG analyzer uses a small whole blood sample in a rotating cup and a pin suspended in the blood by a torsion wire, which is monitored for motion. To speed up the clot formation, a standardized amount of an activator of coagulation (e.g. kaolin, tissue factor) may be added to the cup just before the pin is placed in the cup. The TEG assay is suitable for determining important parameters in the clotting activity (clot initiation time, clot build up dynamics), clot strength (maximum amplitude (MA)) and clot degradation (fibrinolysis). The TEG system's approach to monitoring patient hemostasis is based on the premise that the end result of the hemostatic process is the clot. The clot's physical properties determine whether the patient will have normal hemostasis, or will be at increased risk for hemorrhage or thrombosis.

The term "Multiplate" refers to a commercially available impedance aggregometry based whole blood platelet function analyzer employing anti-coagulated blood. The Multiplate analyzer uses a small whole blood sample in a chamber with two pairs of platinum electrodes. Standardized platelet agonists are added to the blood in the chamber to investigate specific platelet activation/signaling pathways. The Multiplate assay is based on the attachment of platelets on two platinum electrodes, resulting in an increase of electrical resistance between the electrodes. The change of resistance (called impedance) is continuously recorded and is proportional to the amount of platelets sticking to the electrodes and hence proportional to platelet aggregation.

The term "antiadhesive" refers to the effect of compound(s) that reduces the platelets ability to adhere to the endothelium and ultimately form thrombi.

The term "anticoagulant" refers to the effect of compound(s) that reduces or inhibits pro-coagulant coagulation factor activity in the blood and hence reduces or inhibits coagulation of the blood.

The term "antithrombotic" refers to the effect of compound(s) that reduces the platelets ability to aggregate and adhere and interact in the clot building process and hence form thrombi.

The term "antiaggregatory" refers to the effect of compound(s) that reduces the platelets ability to aggregate and interact in the clot building process and hence form thrombi.

The term "coagulopathy" (also called impaired clotting ability, clotting disorder or bleeding disorder) is any defect in the body's mechanism for coagulation and clot building, causing a predisposition either for too slow (hypocoagulability) or too quick (hypercoagulability) clot formation. Clinically, coagulopathy can present with both increased bleeding tendency and increased thromboembolic events/increased risk of thrombosis.

The term "glycocalyx" refers here to the carbohydrate-rich layer which is covering the endothelial cells in healthy individuals. The glycocalyx comprises proteoglycans which can be soluble or linked to the endothelial cell membrane.

The term "organ failure" refers to an altered organ function in an acutely ill patient requiring medical intervention to achieve body homeostasis and/or to compensate for the loss of function from that failing organ. The organs include but are not limited to heart and vessels (cardiac failure, vascular collapse, hypotension, organ failure), lungs (respiratory failure), liver (liver failure), kidneys (renal failure), brain (encephalopathy).

The term "multiple organ failure" (abbreviated MOF) or "multiple organ dysfunction syndrome" (abbreviated MODS) is altered function of more than one organ in an acutely ill patient requiring medical intervention to achieve homeostasis and/or to compensate for the loss of function from the failing organs.

The term "shedding of thrombomodulin" or "release of thrombomodulin" as used herein refers to the process whereby cell-bound thrombomodulin is removed from the cell and becomes soluble in the blood and/or plasma phase of the blood. This event reflects endothelial cell damage.

The term "shedding" of the glycocalyx is herein referred to as degradation of the glycocalyx and release of its components that hereby becomes soluble in the blood and/or plasma phase of the blood.

The term "reperfusion injury" as used herein refers to damage to tissue caused when blood supply returns to the tissue after a period of ischemia. The absence of oxygen and nutrients from blood creates a condition where the restoration of circulation results in inflammation and oxidative damage through the induction of oxidative stress rather than restoration of normal function.

The term "fibrinolysis" means a process wherein a fibrin clot, the product of coagulation, is broken down.

The term "sepsis" is used in the conventional clinical meaning, referring to a whole-body inflammatory state (called systemic inflammatory response syndrome (SIRS)) AND the presence of a known or suspected infection. "Severe sepsis" is defined as sepsis-induced organ dysfunction or tissue hypoperfusion (manifesting e.g. as hypotension, elevated lactate, decreased urine output or altered mental status). "Septic shock" is severe sepsis plus persistently low blood pressure despite the administration of intravenous fluids. Sepsis can lead to severe sepsis, septic shock, multiple organ dysfunction syndrome/multiple organ failure (MODS/MOF) and death.

The term "systemic inflammatory response syndrome" or "SIRS" is used in the conventional clinical meaning, referring to systemic inflammation in response to an insult without confirmed infectious process. SIRS can be diagnosed when 2 or more of the following criteria are present: 1) Body temperature less than 36° C. (96.8° F.) or greater than 38° C. (100.4° F.); 2) Heart rate greater than 90 beats per minute; 3) Tachypnea (high respiratory rate), with greater than 20 breaths per minute or an arterial partial pressure of carbon dioxide less than 4.3 kPa (32 mmHg) and 4) White blood cell count less than 4000 cells/mm$^3$ ($4\times10^9$ cells/L) or greater than 12,000 cells/mm$^3$ ($12\times10^9$ cells/L) or the presence of greater than 10% immature neutrophils (band forms). When an infection is suspected or proven (by culture, stain, or polymerase chain reaction (PCR)), together with SIRS, this is per definition sepsis.

The term "systemic inflammation" is altered organ function in an acutely ill patient due to the nonspecific conserved response of the body (vasculature, immune system, tissues) to infections, non-infectious antigens, trauma, burn, organ/tissue destruction/degeneration/damage, ischemia, haemorrhage, intoxication, and/or malignancy.

The term "ELISA" refers to "Enzyme linked immunosorbent assay". In the ELISA method, bound antigen/antibody (Ab) is detected by an antibody linked (primarily or secondarily) to an enzyme (Ab*) whose activity can be determined. The activity of the Ab* serves as a quantitative estimate of the amount of the investigated antigen/antibody in the biological specimen.

The term "Scoring systems" refers to scoring systems developed to standardize the evaluation of a patient's prognosis (risk of death), disease severity or disease progression. Depending on the score, it is applied at admission, during ICU/hospital stay and/or at specific time-points after admission (e.g. after 6 months). The scores thus provide standardized assessments of mortality risk, morbidity, disease severity, clinical disease progression and outcome.

The term "Injury Severity Score" or "ISS" refers to an anatomical scoring system that provides an overall score for trauma patients with multiple injuries. Each injury is assigned an Abbreviated Injury Scale (AIS) score and is allocated to one of six body regions (Head, Face, Chest, Abdomen, Extremities (including Pelvis), External). Only the highest AIS score in each body region is used. To calculate the ISS score, the 3 most severely injured body regions have their score squared and added together to produce the ISS score: $AISx^2 + AISy^2 + AISz^2 = ISS$. The ISS score takes values from 0 to 75. If an injury is assigned an AIS of 6 (unsurvivable injury), the ISS is automatically assigned to 75. The ISS is virtually the only anatomical scoring system in use and correlates linearly with mortality, morbidity, hospital stay and other measures of severity. The ISS is applied one time at admission but not at later time-points during hospital stay.

The term "Glasgow Coma Scale" or "GCS" score refers to a neurological scoring scale that in an objective way records the conscious state of a patient for initial as well as subsequent assessment. It was initially used to assess the level of consciousness after head injury but the scale is now used by first aid, emergency medical services (EMS), nurses and doctors as being applicable to all acute medical and trauma patients. In hospitals it is also used in monitoring patients while in the intensive care unit (ICU). The GCS is applied at admission and hereafter at any time-point during hospital stay for evaluation of the present level of or changes in consciousness.

The GCS is scored between 3 and 15 (the sum of points given for each of the three evaluation parameters), 3 being the worst, and 15 the best. A GCS of 13 or higher correlates with a mild brain injury, 9-12 is a moderate injury, 8 is a severe brain injury 3 is deep unconsciousness.

GCS is composed of three parameters: Best Eye Response, Best Verbal Response, and Best Motor Response:

| | |
|---|---|
| Best Eye Response (max 4 points) | 1. No eye opening |
| | 2. Eye opening to pain |
| | 3. Eye opening to verbal command |
| | 4. Eyes open spontaneously |
| Best Verbal Response (max 5 points) | 1. No verbal response |
| | 2. Incomprehensible sounds |
| | 3. Inappropriate words |
| | 4. Confused |
| | 5. Orientated |
| Best Motor Response (max 6 points) | 1. No motor response |
| | 2. Extension to pain |
| | 3. Flexion to pain |
| | 4. Withdrawal from pain |
| | 5. Localizing pain |

The term "Simplified Acute Physiology Score II" or "SAPS II" refers to a scoring system designed to measure the severity of disease for patients ≥15 years admitted to Intensive Care Units (ICU).

The measurement has to be completed 24 hours after admission to the ICU, resulting in an integer point score (sum of worst value sub-scores) between 0 and 163 and a predicted mortality between 0% and 100% (mortality corresponding to 10%, 25%, 50%, 75% and 90% in patients with a score or 29, 40, 52, 64 and 77, respectively). No new score can be calculated during the ICU stay, but if a patient is discharged from the ICU and readmitted, a new SAPS II score can be calculated.

The score is based on the worst value of the following physiologic parameters within the past 24 hours:

| Parameter | Unit | Score |
|---|---|---|
| Age | years | |
| Heart Rate | bpm | |
| Systolic Blood Pressure | mmHg | |
| Temperature | ° C. or F. | |
| Glasgow Coma Scale | score | |
| Mechanical Ventilation or CPAP | yes, no | |
| PaO$_2$ | mmHg | |
| FiO$_2$ | % | |
| Urine Output | ml | |

| Parameter | Unit | Score |
|---|---|---|
| Blood Urea Nitrogen | mg/dl | |
| Sodium | mEq/l | |
| Potassium | mEq/l | |
| Bicarbonate | mEq/l | |
| Bilirubin | mg/dl | |
| White Blood Cell | ×10$^9$/l | |
| Chronic diseases | metastatic cancer, hematologic malignancy or AIDS | |
| Type of admission | scheduled surgical, medical or unscheduled surgical | |
| Sum | | X points |

The term "Sequential Organ Failure Assessment" or "SOFA" score refers to a scoring system applied to determine the extent of a person's organ function or degree of organ failure. The score is based on six different sub-scores, one each for the respiratory, cardiovascular, hepatic, coagulation, renal and neurological systems. The point given for each sub-score is summed up to give the total SOFA score. The score is typically determined at admission to ICU and hereafter daily to evaluate disease progression. The score is applicable to all types of ICU patients including trauma, sepsis, resuscitated cardiac arrest patients, major surgery etc.

| Organ system | Parameter | SOFA sup-score points | | | |
|---|---|---|---|---|---|
| | | 1 | 2 | 3 | 4 |
| Nervous | GCS | 13-14 | 10-12 | 6-9 | <6 |
| Respiratory | PaO2/FiO2 [mmHg] | <400 | <300 | <200 AND ventilator | <100 AND ventilator |
| Cardiovascular | MAP [mmHg] and/or vasopressor (dop, epi, nor) | MAP <70 | dop ≤5 OR dob (any dose) | dop >5 OR epi ≤0.1 OR nor ≤0.1 | dop >15 OR epi >0.1 OR nor >0.1 |
| Renal | Creatinine [μmol/l] or urine output | 110-170 | 171-299 | 300-440 OR <500 ml/d | >440 OR <200 ml/d |
| Liver | Bilirubin [μmol/l] | >20-32 | >33-101 | >102-204 | >204 |
| Coagulation | Platelet count [10$^9$/l] | <150 | <100 | <50 | <20 |

The term "Cerebral Performance Category" or "CPC" refers to a scale to determine neurological outcome after cardiac arrest. The CPC is applied at any time after the cardiac arrest at a minimum of standardized time-points. The patient is scored from 1-5 depending on the clinical presentation.

| | |
|---|---|
| CPC 1 | Good cerebral performance: conscious, alert, able to work, might have mild neurologic or psychological deficit |
| CPC 2 | Moderate cerebral disability: conscious, sufficient cerebral function for independent activities of daily life. Able to work in sheltered environment. |
| CPC 3 | Severe cerebral disability: conscious, dependent on others for daily support because of impaired brain function. Ranges from ambulatory state to severe dementia or paralysis. |
| CPC 4 | Coma |
| CPC 5 | Brain death: apnea, areflexia, EEG silence, etc. |

The term "Modified Rankin Scale" or "mRS" refers to a commonly used scale for measuring the degree of disability or dependence in the daily activities of people who have suffered a stroke, cardiac arrest, or other causes of neurological disability. The patient is scored from 1-6 depending on the clinical presentation.

| | |
|---|---|
| mRS 1 | No symptoms at all |
| mRS 2 | No significant disability. Able to carry out all usual activities, despite some symptoms. |
| mRS 3 | Slight disability. Able to look after own affairs without assistance, but unable to carry out all previous activities. |
| mRS 4 | Moderate disability. Requires some help, but able to walk unassisted. |
| mRS 5 | Severe disability. Requires constant nursing care and attention, bedridden, incontinent. |
| mRS 6 | Dead |

The term "APACHE" or "APACHE II score", refers to Acute Physiology and Chronic Health Evaluation (APACHE) II score. APACHE II is a scoring system designed to measure the severity of disease for patients ≥15 years admitted to Intensive Care Units (ICU). The measurement must be completed 24 hours after admission to the ICU, resulting in an integer point score (based on the worst value sub-scores) between 0 and 71. Higher scores correspond to more severe disease and a higher risk of death. The APACHE II score cannot be directly converted to a percent risk of mortality but can be used to calculate a mortality risk if the patient's indication for ICU admission is accounted for. No new score can be calculated during the ICU stay but if a patient is discharged from the ICU and readmitted, a new APACHE II score can be calculated. The score is based on the worst value of the following physiologic parameters within the past 24 hours:

| Parameter | Unit | Score |
|---|---|---|
| Age | Years | |
| Glasgow Coma Scale | Score | |
| Temperature | ° C. of F. | |
| Mean Arterial Blood (MAP) Pressure | mmHg | |
| Heart Rate | bpm | |
| Respiratory Rate | bpm | |
| FiO$_2$ | % | |
| PaO$_2$ | mmHg | |
| Sodium | mEq/l | |
| Potassium | mEq/l | |
| Creatinine | Mg/dl | |
| Acute Renal Failure | yes, no | |
| Hematocrit | % | |
| White Blood Cell | ×10$^9$/l | |
| Severe organ system insufficiency or is immunocompromised? | Liver: Biopsy-proven cirrhosis with portal hypertension; episodes of past upper GI bleeding attributed to portal hypertension; or prior episodes of hepatic failure, encephalopathy, or coma. Cardiovascular: New York Heart Association (NYHA) class IV heart failure. Respiratory: Chronic restrictive, obstructive, or vascular disease resulting in severe exercise restriction (ie, unable to climb stairs or perform household duties); documented chronic hypoxia, hypercapnia, secondary polycythemia, severe pulmonary hypertension (>40 mmHg); or respirator dependency. | |

-continued

| Parameter | Unit | Score |
|---|---|---|
| | Renal: Receiving chronic dialysis. Immunocompromised: The patient has received therapy that suppresses resistance to infection (e.g., immune-suppression, chemotherapy, radiation, long-term or high-dose steroids, or advanced leukemia, lymphoma, or AIDS) | |
| SUM | | X points |

SUMMARY

The embodiments are disclosed in the present description, drawings and in the claims. In particular, embodiments disclosed in the examples of the present disclosure are considered particularly preferred.

The aspects of the disclosed embodiments relate to a method of diagnosing, uses of thrombomodulin as a biological marker, a method of treatment; prostacyclin or an analogue thereof for use in novel treatments and compositions comprising prostacyclin or an analogue thereof for use in novel treatments, all according to the embodiments described in this section in particular, and throughout the present disclosure.

In a first aspect and implementation there is disclosed a method of diagnosing for an individual diagnosed with an acute critical illness, if the individual is a candidate for combination treatment of standard care for the acute critical illness in combination with administration of prostacyclin or an analogue thereof, the method comprising:
  measuring a baseline concentration of soluble thrombomodulin in blood or plasma of the individual;
  determining if the baseline concentration of soluble thrombomodulin in blood or plasma is above a threshold level of at least 2.5 ng/ml; and
  diagnosing the individual as a candidate for combination treatment if the baseline concentration is above the threshold level.

In a second implementation of the first aspect and implementation there is disclosed a method according to the first aspect and implementation wherein the threshold level is at least 4 ng/ml.

In a third implementation of the first aspect and implementation there is disclosed a method according to either the first or the second implementations of the first aspect wherein the method is a method of diagnosing severe endothelial damage in the individual diagnosed with the acute critical illness; wherein the individual is diagnosed with severe endothelial damage in addition to the acute critical illness, if the baseline concentration is above the threshold level.

In a fourth implementation of the first aspect and implementation there is disclosed a method according to any of the first to third implementations wherein the method is a method of diagnosing systemic endotheliopathic syndrome in an individual diagnosed with an acute critical illness; wherein the individual is diagnosed with systemic endotheliopathic syndrome when the individual is diagnosed with both an acute critical illness and severe endothelial damage.

In a second aspect and first implementation thereof there is disclosed the use of thrombomodulin as a biological marker in a method of diagnosing for an individual diagnosed with an acute critical illness, if the individual is a candidate for combination treatment with standard care for the acute critical illness in combination with administration of prostacyclin or an analogue thereof, the method comprising:

measuring a baseline concentration of soluble thrombomodulin in blood or plasma of the individual;

determining if the baseline concentration of soluble thrombomodulin in blood or plasma is above a threshold level of at least 2.5 ng/ml; and diagnosing the individual as a candidate for combination treatment if the baseline concentration is above the threshold level.

In a second implementation of the second aspect and first implementation thereof there is disclosed a use according to the second aspect and first implementation thereof wherein the threshold level is at least 4 ng/ml.

In a third implementation of the second aspect and first implementation thereof there is disclosed a use according to either the first or second implementations of the second aspect wherein the method is a method of diagnosing severe endothelial damage in the individual diagnosed with the acute critical illness; wherein the individual is diagnosed with severe endothelial damage in addition to the acute critical illness, if the baseline concentration is above the threshold level.

In a fourth implementation of the second aspect and first implementation thereof there is disclosed a use according to any of the first to third implementations of the second aspect wherein the method is a method of diagnosing systemic endotheliopathic syndrome in an individual diagnosed with an acute critical illness; wherein the individual is diagnosed with systemic endotheliopathic syndrome when the individual is diagnosed with both an acute critical illness and severe endothelial damage.

In a third aspect and first implementation thereof there is disclosed a method of treating an acute critical illness in an individual diagnosed with the acute critical illness and concurrent increase in a measured thrombomodulin level in blood or plasma of the individual, the method comprising:

(a) measuring a baseline concentration of soluble thrombomodulin in blood or plasma of the individual;

(b) determining if the baseline concentration of soluble thrombomodulin in blood or plasma is above a threshold level of at least 2.5 ng/ml;

(c) administering a dose of 0.5-4 ng/kg/min of prostacyclin or an analogue thereof to the individual continuously for a first time period if the baseline concentration of soluble thrombomodulin in blood or plasma is above the threshold level of at least 2.5 ng/ml;

(d) measuring at the end of the first time period a concentration of soluble thrombomodulin in blood or plasma of the individual;

(e) determining if the concentration of soluble thrombomodulin is lower by at least a decrease of 10% compared to the baseline concentration of thrombomodulin determined prior to initiation of the prostacyclin administration;

(f) assessing if a clinical improvement of the acute critical illness in the individual has occurred during the first time period; and (g) if both a concentration reduction and a clinical improvement is observed, ceasing prostacyclin administration while continuing standard care for the acute critical illness; or (h) otherwise continue prostacyclin administration for a second time period not exceeding the first time period wherein the steps (d) to (h) are repeated until ceasing prostacyclin administration to the individual following step (g).

In a second implementation of the third aspect and first implementation thereof there is disclosed a method according to the first implementation wherein the threshold level is at least 4 ng/ml.

In a third implementation of the third aspect and first implementation thereof there is disclosed a method according to either the first or second implementations wherein the dose is 1-2 ng/kg/min.

In a fourth implementation of the third aspect and first implementation thereof there is disclosed a method according to any of the first to third implementations wherein the analogue of prostacyclin is either Iloprost or Flolan.

In a fifth implementation of the third aspect and first implementation thereof there is disclosed a method according to any of the first to fourth implementations wherein the first time period is at least 48 hours or at least 72 hours.

In a sixth implementation of the third aspect and first implementation thereof there is disclosed a method according to any of the first to fifth implementations wherein the second time period is 12 hours or 24 hours.

In a seventh implementation of the third aspect and first implementation thereof there is disclosed a method according to any of the first to sixth implementations wherein in step (e) the decrease is at least 20%.

In an eight implementation of the third aspect and first implementation thereof there is disclosed a method according to any of the first to seventh implementations wherein the baseline concentration is measured immediately after or shortly after recognition of the acute critical illness.

In a ninth implementation of the third aspect and first implementation thereof there is disclosed a method according to the first to eight implementations wherein the baseline concentration is measured within 5 minutes and up to 6 hours after recognition of the acute critical illness.

In a tenth implementation of the third aspect and first implementation thereof there is disclosed a method according to any of the first to ninth implementations wherein the prostacyclin administration is initiated immediately or shortly after a completion of step (b) has determined that the baseline concentration of soluble thrombomodulin in blood or plasma is above the threshold level.

In an eleventh implementation of the third aspect and first implementation thereof there is disclosed a method according to the tenth implementation wherein the prostacyclin administration is initiated within 5 min to 12 hours after a completion of step (b) has determined that the baseline concentration of soluble thrombomodulin in blood or plasma is above the threshold level.

In a twelfth implementation of the third aspect and first implementation thereof there is disclosed a method according to any of the first to eleventh implementations wherein prostacyclin or an analog thereof is administered as according to step (c) prior to steps (a) and (b) having been completed.

In a thirteenth implementation of the third aspect and first implementation thereof there is disclosed a method according to any of the first to twelfth implementations wherein the concurrent increase in a measured thrombomodulin level in blood or plasma of the individual is the result of severe endothelial damage.

In a fourteenth implementation of the third aspect and first implementation thereof there is disclosed a method according to any of the first to thirteenth implementations wherein the concurrent increase in a measured thrombomodulin level in blood or plasma of the individual is the result of systemic endotheliopathic syndrome.

In a fifteenth implementation of the third aspect and first implementation thereof there is disclosed a method according to any of the first to fourteenth implementations wherein the acute critical illness is selected from trauma, burn injury trauma, sepsis, severe sepsis, septic shock, acute myocardial infarction, cardiac arrest, systemic inflammatory response syndrome (SIRS), acute major surgery, anti-shock therapy, or a thromboembolic event.

In a sixteenth implementation of the third aspect and first implementation thereof there is disclosed a method according to any of the first to fifteenth implementations wherein prostacyclin administration is by intravenous infusion.

In a fourth aspect and first implementation thereof there is disclosed prostacyclin or an analogue thereof for use in the treatment of an acute critical illness, the treatment according to any of the first to sixteenth implementations of the third aspect.

In a fifth aspect and first implementation thereof there is disclosed a composition comprising prostacyclin or an analogue thereof for use in the treatment of an acute critical illness, the treatment according to any of the first to sixteenth embodiments of the third aspect.

In a sixth aspect and a first implementation thereof there is disclosed a method of diagnosing for an individual diagnosed with an acute critical illness, if the individual is a candidate for combination treatment of standard care for the acute critical illness in combination with administration of prostacyclin or an analogue thereof, the method comprising: measuring a baseline concentration of syndecan-1 in blood or plasma of the individual;
determining if the baseline concentration of syndecan-1 in blood or plasma is above a threshold level of at least 40 ng/ml; and diagnosing the individual as a candidate for combination treatment if the baseline concentration is above the threshold level.

In a second implantation of the sixth aspect the threshold level for syndecan-1 is at least 60 ng/ml.

In a seventh aspect and a first implementation thereof there is disclosed a method of treating an acute critical illness in an individual diagnosed with the acute critical illness and concurrent increase and a measured syndecan-1 level in blood or plasma of the individual, the method comprising:
(a) measuring a baseline concentration of syndecan-1 in blood or plasma of the individual;
(b) determining if the baseline concentration of syndecan-1 in blood or plasma is above a threshold level of at least 40 ng/ml;
(c) administering a dose of 0.5-4 ng/kg/min of prostacyclin or an analogue thereof to the individual continuously for a first time period if the baseline concentration of syndecan-1 in blood or plasma is above the threshold level of at least 40 ng/ml;
(d) measuring at the end of the first time period a concentration of soluble thrombomodulin in blood or plasma of the individual;
(e) determining if the concentration of soluble thrombomodulin is lower by at least a decrease of 10% compared to a measured baseline concentration of thrombomodulin determined prior to initiation of the prostacyclin administration;
(f) assessing if a clinical improvement of the acute critical illness in the individual has occurred during the first time period; and
(g) if both a concentration reduction and a clinical improvement is observed, ceasing prostacyclin administration while continuing standard care for the acute critical illness; or
(h) otherwise continue prostacyclin administration for a second time period not exceeding the first time period wherein the steps (d) to (h) are repeated until ceasing prostacyclin administration to the individual following step (g).

In a second implantation of the seventh aspect the threshold level for syndecan-1 is at least 60 ng/ml.

In an eighth aspect and a first implementation thereof there is disclosed a method of diagnosing for an individual diagnosed with an acute critical illness, if the individual is a candidate for combination treatment of standard care for the acute critical illness in combination with administration of prostacyclin or an analogue thereof, the method comprising: measuring a baseline concentration of adrenaline in blood or plasma of the individual;
determining if the baseline concentration of syndecan-1 in blood or plasma is above a threshold level of at least 225 pg/ml; and diagnosing the individual as a candidate for combination treatment if the baseline concentration is above the threshold level.

In a second implantation of the eighth aspect the threshold level for adrenaline is at least 300 pg/ml.

In a ninth aspect and a first implementation thereof there is disclosed a method of treating an acute critical illness in an individual diagnosed with the acute critical illness and concurrent increase and a measured adrenaline level in blood or plasma of the individual, the method comprising:
(i) measuring a baseline concentration of adrenaline in blood or plasma of the individual;
(j) determining if the baseline concentration of adrenaline in blood or plasma is above a threshold level of at least 225 pg/ml;
(k) administering a dose of 0.5-4 ng/kg/min of prostacyclin or an analogue thereof to the individual continuously for a first time period if the baseline concentration of adrenaline in blood or plasma is above the threshold level of at least 225 pg/ml;
(l) measuring at the end of the first time period a concentration of soluble thrombomodulin in blood or plasma of the individual;
(m) determining if the concentration of soluble thrombomodulin is lower by at least a decrease of 10% compared to a measured baseline concentration of thrombomodulin determined prior to initiation of the prostacyclin administration;
(n) assessing if a clinical improvement of the acute critical illness in the individual has occurred during the first time period; and
(o) if both a concentration reduction and a clinical improvement is observed, ceasing prostacyclin administration while continuing standard care for the acute critical illness; or
(p) otherwise continue prostacyclin administration for a second time period not exceeding the first time period wherein the steps (d) to (h) are repeated until ceasing prostacyclin administration to the individual following step (g).

In a second implantation of the ninth aspect wherein the threshold level for adrenaline is at least 300 pg/ml.

In a tenth aspect and a first implementation thereof there is disclosed a method of treating an acute critical illness in an individual diagnosed with the acute critical illness and concurrent increase in a measured thrombomodulin level in blood or plasma of the individual, the method comprising:

(a) measuring a baseline concentration of soluble thrombomodulin in blood or plasma of the individual;
(b) determining if the baseline concentration of soluble thrombomodulin in blood or plasma is above a threshold level of at least 2.5 ng/ml;
(c) administering a dose of 0.5-4 ng/kg/min of prostacyclin or an analogue thereof to the individual;

In an eleventh aspect and a first implementation thereof there is disclosed a method of treating an acute critical illness in an individual diagnosed with the acute critical illness and concurrent increase in a measured syndecan-1 level in blood or plasma of the individual, the method comprising:
(d) measuring a baseline concentration of syndecan-1 in blood or plasma of the individual;
(e) determining if the baseline concentration of syndecan-1 in blood or plasma is above a threshold level of at least 40 ng/ml;
(f) administering a dose of 0.5-4 ng/kg/min of prostacyclin or an analogue thereof to the individual;

In a twelfth aspect and a first implementation thereof there is disclosed a method of treating an acute critical illness in an individual diagnosed with the acute critical illness and concurrent increase in a measured adrenaline level in blood or plasma of the individual, the method comprising:
(g) measuring a baseline concentration of adrenaline in blood or plasma of the individual;
(h) determining if the baseline concentration of adrenaline in blood or plasma is above a threshold level of at least 225 pg/ml;
(i) administering a dose of 0.5-4 ng/kg/min of prostacyclin or an analogue thereof to the individual;

In a further implementation of any one of the first, second, third and sixth to twelfth aspect the measurement of thrombomodulin, syndecan-1, adrenaline or VEGF is conducted by a point-of-care (POC) assay.

DESCRIPTION OF DRAWINGS AND TABLES

FIG. 1 shows a schematic presentation of the systemic endotheliopathic syndrome at the vascular level.

FIG. 1 is a schematic presentation of systemic endotheliopathic syndrome illustrating, at the vascular level, how an acute critically ill patient with an increasing injurious hit will experience progressive damage to the endothelium resulting in endothelial shedding/release of thrombomodulin and ensuing increases in circulating soluble thrombomodulin (sTM, bubbles). Progressive endothelial damage will clinically result in impaired vascular barrier function, capillary leakage, bleeding, hypotension, multiple organ failure and ultimately death.

FIG. 2a shows a graph of a soluble thrombomodulin (ng/ml) at baseline (0 h), at the end of (2 h) and after (4 h, 5 h, 6 h, 8 h, 24 h) 2 hours 4 ng/kg/min Flolan® infusion in healthy volunteers. *, significant difference from baseline.

FIG. 2b shows a graph of protein C (%) at baseline (0 h), at the end of (2 h) and after (4 h, 5 h, 6 h, 8 h, 24 h) 2 hours 4 ng/kg/min Flolan® infusion in healthy volunteers. *, significant difference from baseline.

FIG. 2c shows a graph of plasminogen activator inhibitor (PAI)-1 (ng/ml) at baseline (0 h), at the end of (2 h) and after (4 h, 5 h, 6 h, 8 h, 24 h) 2 hours 4 ng/kg/min Flolan® infusion in healthy volunteers. *, significant difference from baseline.

FIG. 2d shows a graph of antithrombin (microg/ml) at baseline (0 h), at the end of (2 h) and after (4 h, 5 h, 6 h, 8 h, 24 h) 2 hours 4 ng/kg/min Flolan® infusion in healthy volunteers. *, significant differences from baseline.

FIG. 3a shows a graph of soluble thrombomodulin (ng/ml) at baseline (baseline), during (30 min), at the end of (2 h) and after (2 h post) 2 hours 1 ng/kg/min Ilomedin® infusion in healthy volunteers. *, significant difference from baseline; (*), borderline significant difference from baseline.

FIG. 3b shows a graph of protein C (%) at baseline (baseline), during (30 min), at the end of (2 h) and after (2 h post) 2 hours 1 ng/kg/min Ilomedin® infusion in healthy volunteers. *, significant difference from baseline; (*), borderline significant difference from baseline.

FIG. 3c shows a graph of prostacyclin (pg/ml) at baseline (baseline), during (30 min), at the end of (2 h) and after (2 h post) 2 hours 1 ng/kg/min Ilomedin® infusion in healthy volunteers. *, significant difference from baseline; ‡, significant difference from previous time-point.

Figure 4:
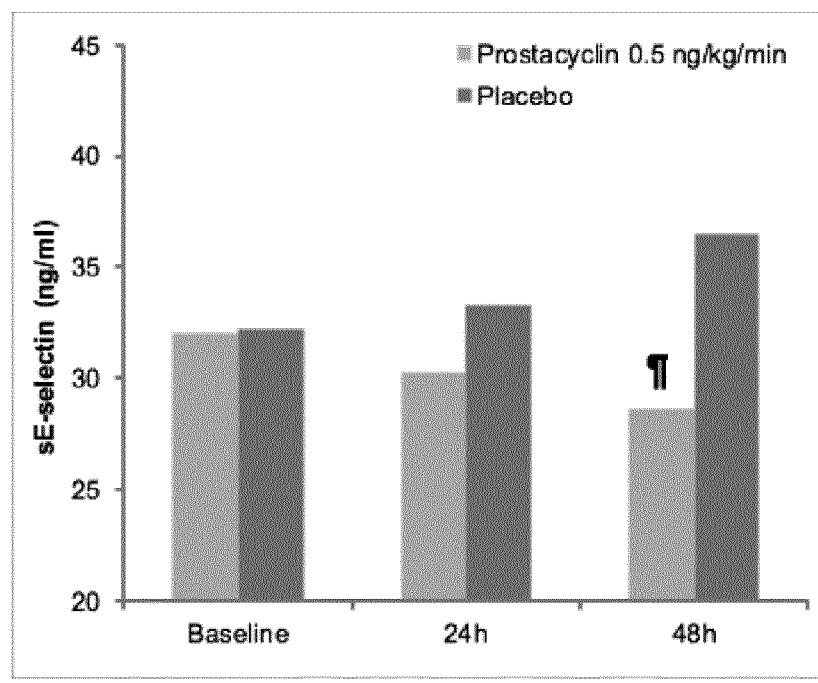

FIG. 4 is a graph showing test results that illustrates the effect of Ilomedin infusion in patients with acute myocardial infarction undergoing percutaneous coronary intervention FIG. 4 shows a graph illustrating soluble E-selectin (ng/ml) at baseline (baseline), at the end of 24 hours (24 h) and after (48 h) 24 hours active (0.5 ng/kg/min Ilomedin® infusion) or placebo (0.9% saline infusion) therapy of AMI PCI patients. ¶, significant difference between active and placebo group.

Figure 5A:
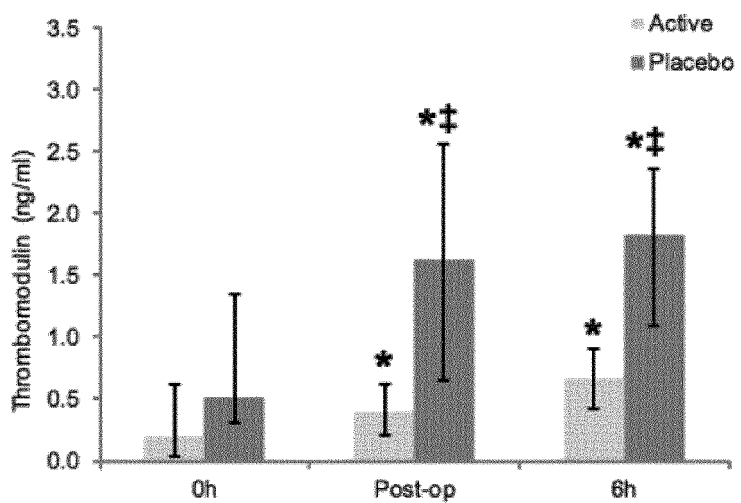
Figure 5B:
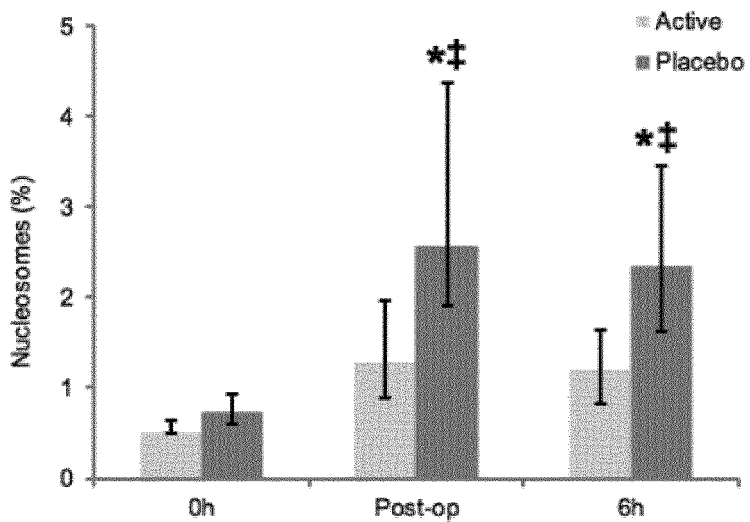
Figure 5C:
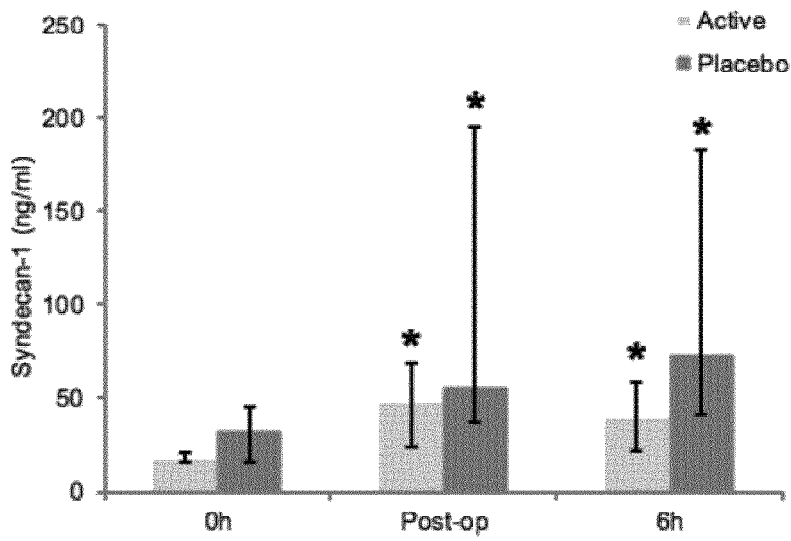

FIGS. 5a-5c are graphs showing test results that illustrate the effect of Ilomedin infusion in patients undergoing Whipple surgery.

FIG. 5a shows a graph illustrating soluble thrombomodulin (ng/ml) pre-operative (0 h), post-operative (post-op) and 6 hours post-operatively (6 h) intra- and post-operative active (1 ng/kg/min Ilomedin® infusion) or placebo (0.9% saline infusion) therapy of Whipple patients. *, significant difference from baseline; ‡, significant difference between active and placebo group.

FIG. 5b shows a graph illustrating nucleosomes (%) pre-operative (0 h), post-operative (post-op) and 6 hours post-operatively (6 h) intra- and post-operative active (1 ng/kg/min Ilomedin® infusion) or placebo (0.9% saline infusion) therapy of Whipple patients. *, significant difference from baseline; ‡, significant difference between active and placebo group.

FIG. 5c shows a graph illustrating syndecan-1 (ng/ml) pre-operative (0 h), post-operative (post-op) and 6 hours post-operatively (6 h) intra- and post-operative active (1 ng/kg/min Ilomedin® infusion) or placebo (0.9% saline infusion) therapy of Whipple patients. *, significant difference from baseline.

Figure 6:
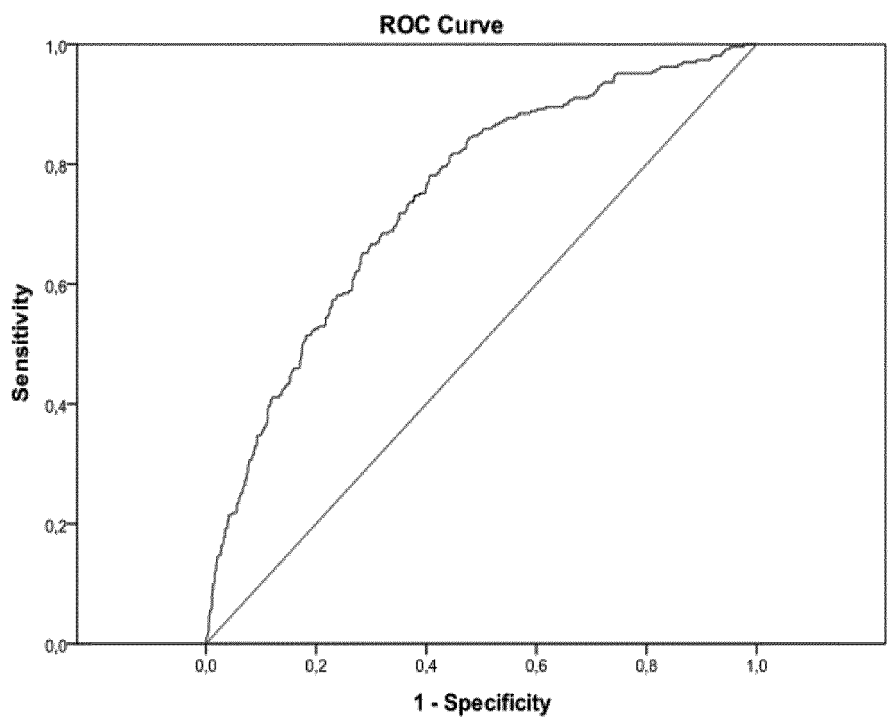

FIG. 6 shows a graph illustrating a receiver operating characteristic (ROC)-curve of thrombomodulin for predicting mortality in acute critically ill patients suffering from trauma, myocardial infarction, cardiac arrest, sepsis/severe sepsis/septic shock. Thrombomodulin AUC for predicting 28-day mortality: AUC 0.744 (0.712-0.776), $p<0.0001$. Highest Youden Index reveals a threshold level of 4.0 ng/ml thrombomodulin in plasma. Sensitivity 0.781, 1-specificity 0.407.

Figure 7:
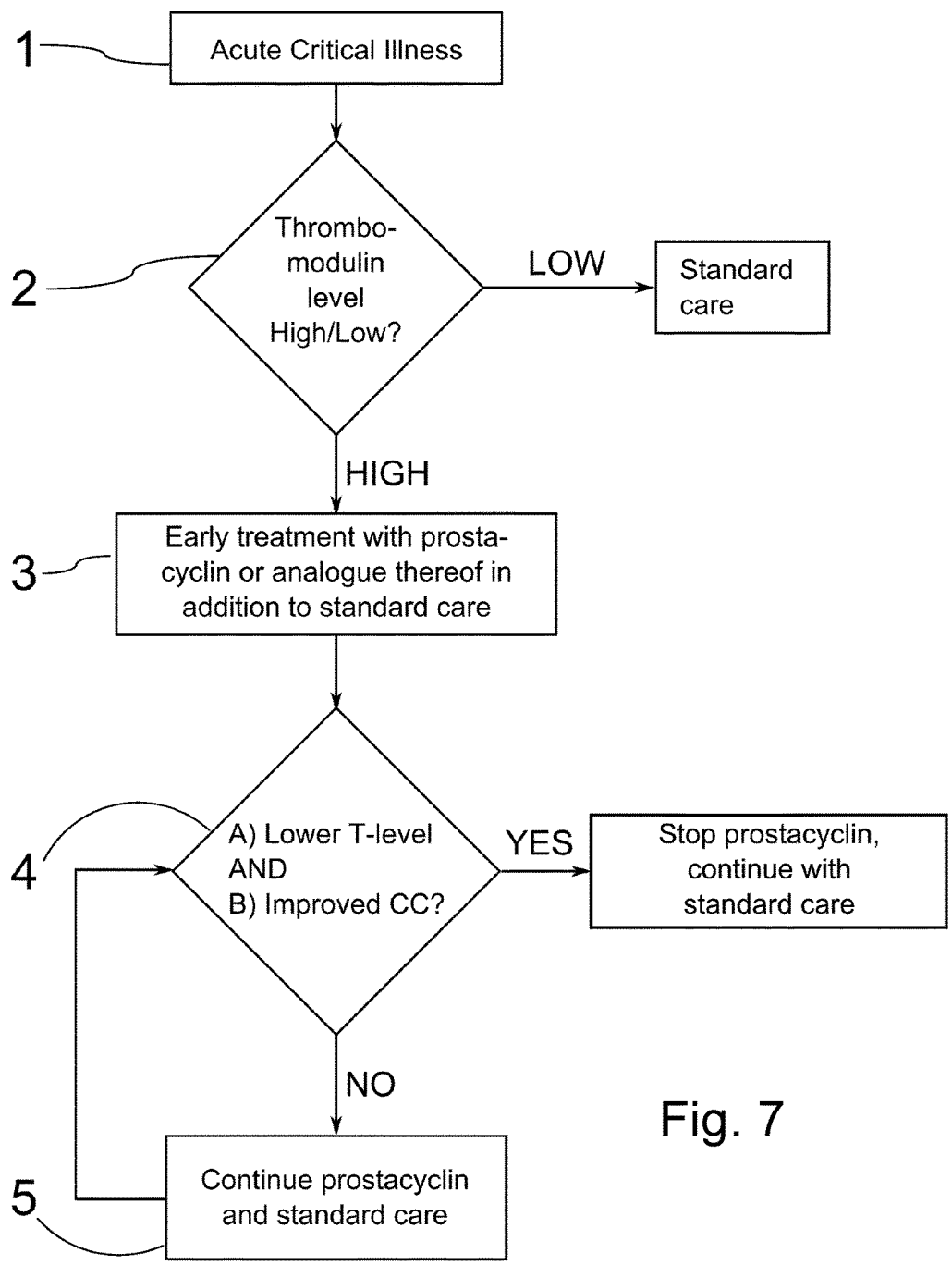

FIG. 7 shows a flow diagram illustrating an example embodiment of a method for deciding on treatment with prostacyclin or an analogue thereof in patients presenting with acute critically illness in combination with high levels of thrombomodulin.

Figure 8:
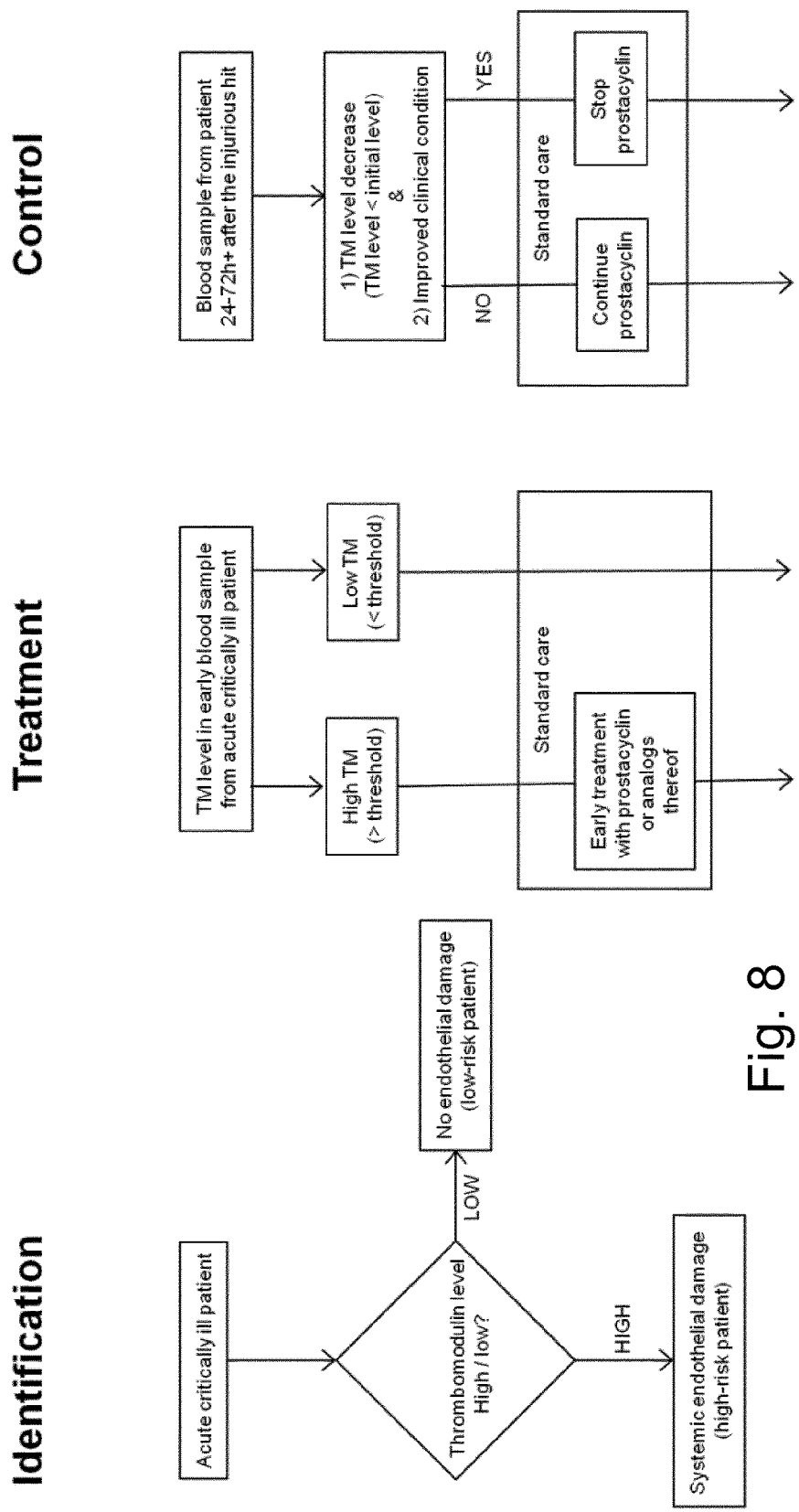

FIG. 8 shows a flow diagram illustrating the invention as exemplary described in FIG. 7 in terms of its constituent units of identification, treatment and control.

Figure 9A:
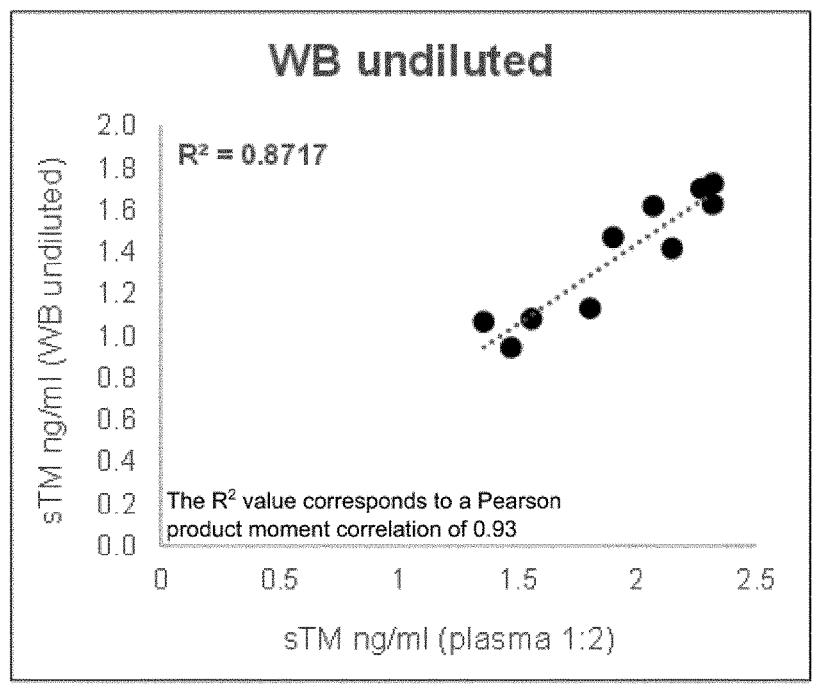
Figure 9B:
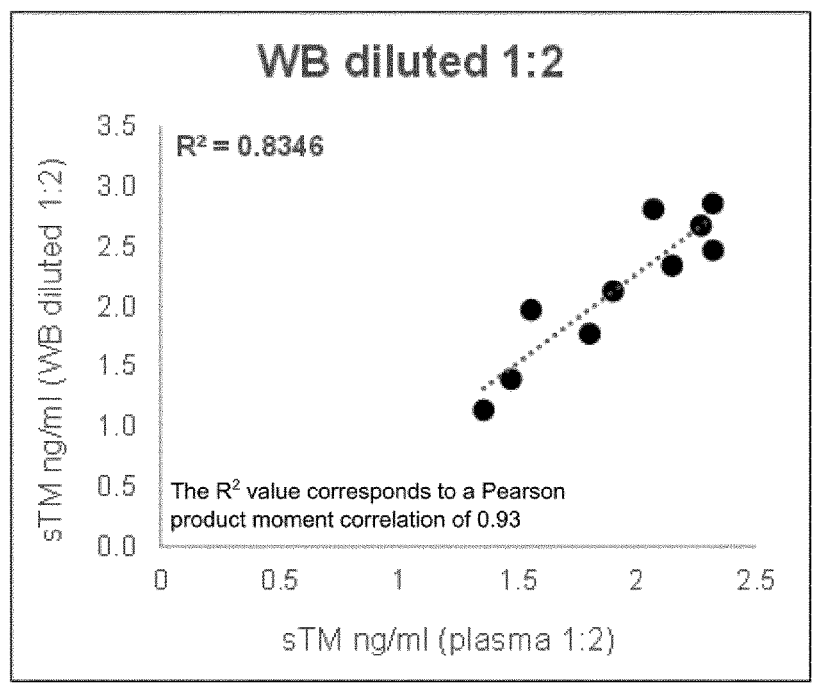
Figure 9C:
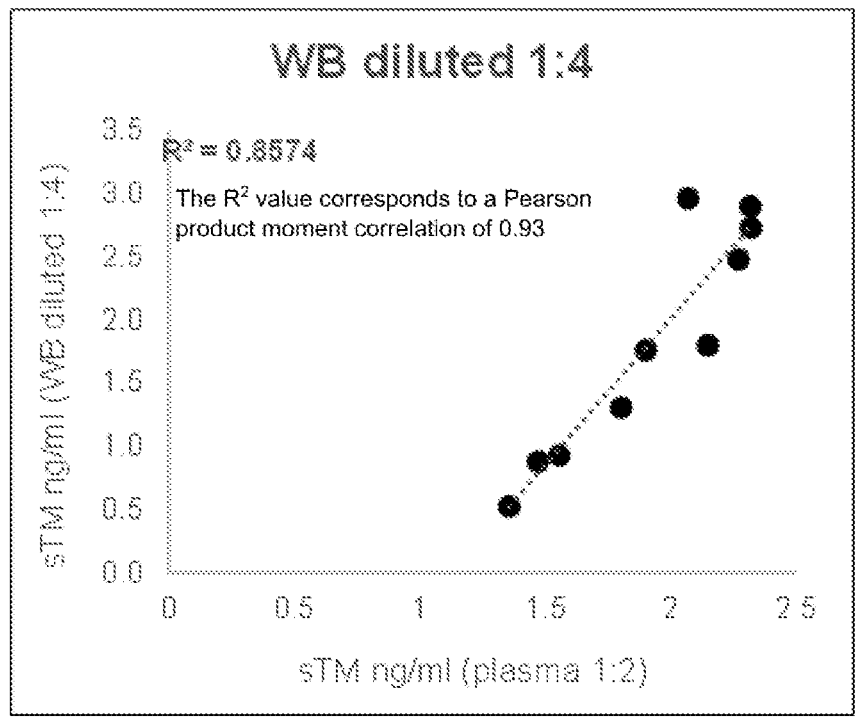

FIG. 9 shows ELISA scores for thrombomodulin in blood versus plasma. Correlations between thrombomodulin concentrations (ng/ml) measured in 1:2 diluted plasma (golden standard) and whole blood, either undiluted (FIG. 9a), diluted 1:2 (FIG. 9b), or diluted 1:4 (FIG. 9c).

Figure 10:
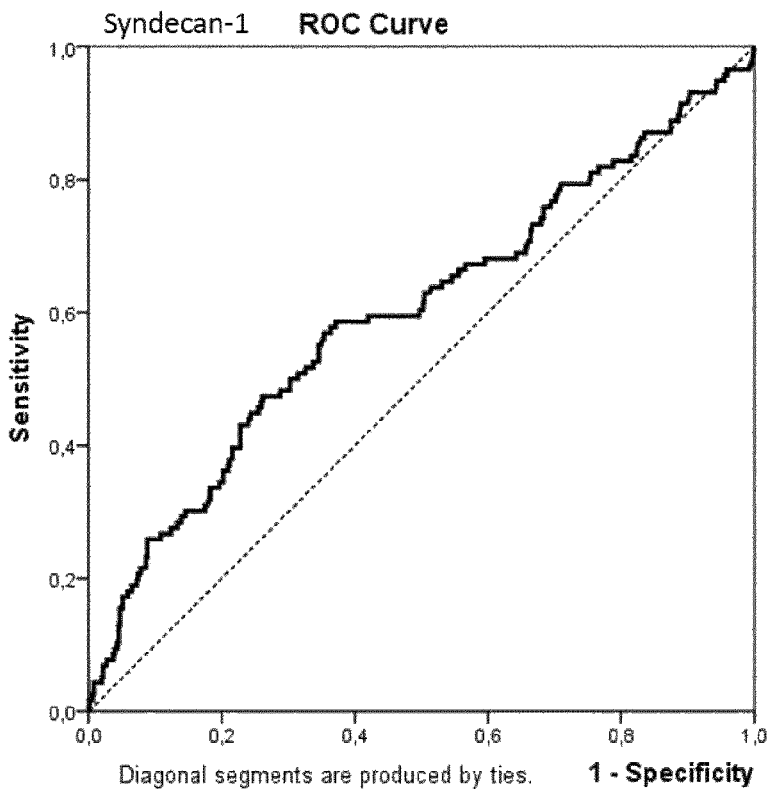

FIG. 10 shows a graph illustrating a receiver operating characteristic (ROC)-curve of syndecan-1.

Figure 11:
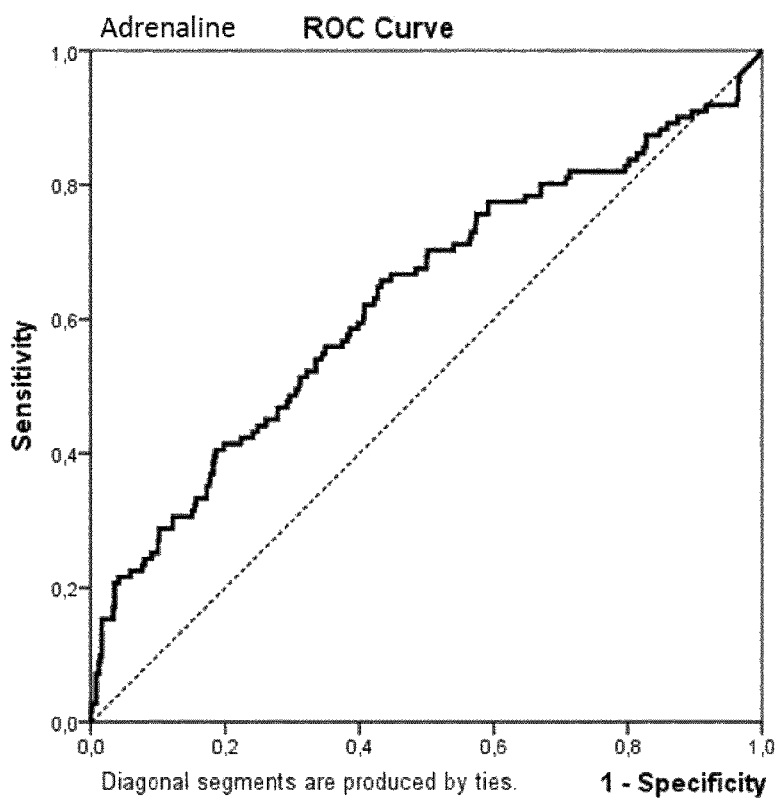

FIG. 11 shows a graph illustrating a receiver operating characteristic (ROC)-curve of adrenaline.

FIG. 12 shows Table 1, which details a study of demography and disease severity in ICU patients.

FIG. 13 shows Table 2, which details a study of median thrombomodulin levels in plasma/serum (ng/ml) in 2,118 acute critically ill patients FIG. 14 shows Table 3, which details a study of the thrombomodulin level versus test sensitivity for the patient group of Table 2.

FIG. 15 shows Table 4a, which details results for trauma patients. Table 4a details results for injury severity at admission in 635 trauma patients dependent on the level of sTM (soluble thrombomodulin).

FIG. 16 shows Table 4b, which details results based on 270 trauma patients.

FIG. 17 shows Table 5a, which details results for cardiac arrest patients based on n=169 patients resuscitated from cardiac arrest. FIG. 17 Table 5a details the proportion of OHCA patients with sTM>2.5-5-5 ng/ml at admission.

FIG. 18 shows Table 5b, which details the absolute and proportional (median) changes in sTM from admission and 24 h and 72 h onward in 28 day survivors and non-survivors.

FIG. 19 shows Table 5c, which details the predictive value of sTM at different time-points for poor cognitive outcome (CPC≥3/mRS≥4) evaluated by ROC analysis.

FIG. 20 shows Table 6, which details results based on 571 STEMI patients on the proportion of OHCA patients with sTM>2.5-5-5 ng/ml at ICU admission.

FIG. 21 shows Table 7, which details results based on two different cohorts (n=749 and n=184) of patients with sepsis/severe sepsis/septic shock showing the proportion of septic patients with sTM>2.5-5-5 ng/ml at ICU admission.

FIG. 22 shows Table 8, which details a study of demography data and thrombomodulin levels in plasma and whole blood from 10 healthy volunteers.

FIGS. 23 and 24 show Table 9 and 10, respectively, which detail the sensitivities and 1-specificities for predicting mortality are obtained (data from 635 trauma patients) when applying other cut-offs than 40 ng/ml for syndecon-1 and 225 pg/ml for adrenaline,

DETAILED DESCRIPTION

The aspects of the disclosed embodiments relate to the treatment of acute critically ill patients. Patients that are acute critically ill suffer from e.g. severe trauma including burn injury, severe infection including sepsis and septic shock, acute myocardial infarction, resuscitated cardiac arrest, major surgery and/or other conditions that require organ supportive care/intensive care therapy to survive i.e. ventilator therapy, continuous fluid infusion or blood transfusion, vasopressor therapy etc.

The inventors have discovered that some acute critically ill patients, independent of the type of injurious hit, display evidence of a common unifying medical condition that is associated with increased mortality. In prior research papers, e.g. [Johansson and Ostrowski, 2010], the present inventors have suggested that this common unifying medical condition is a distinct diagnosis which the inventors have now labelled systemic endothelial damage.

Based on their findings in thousands acute critically ill patients, the inventors discovered that a large fraction of these patients presented with systemic endothelial damage that across all patients was the strongest marker for mortality. The combination of acute critical illness and systemic endothelial damage has been suggested by the present inventors to represent a novel disease entity which the inventors now label systemic endotheliopathic syndrome, characterized by impaired vascular barrier function and capillary leakage, bleeding, hypotension, multiple organ failure and death in acute critically ill patients [Johansson and Ostrowski 2010]. A patient is considered to have systemic endotheliopathic syndrome when the patient suffers from acute critical illness AND is diagnosed with systemic endothelial damage.

Figure 1:
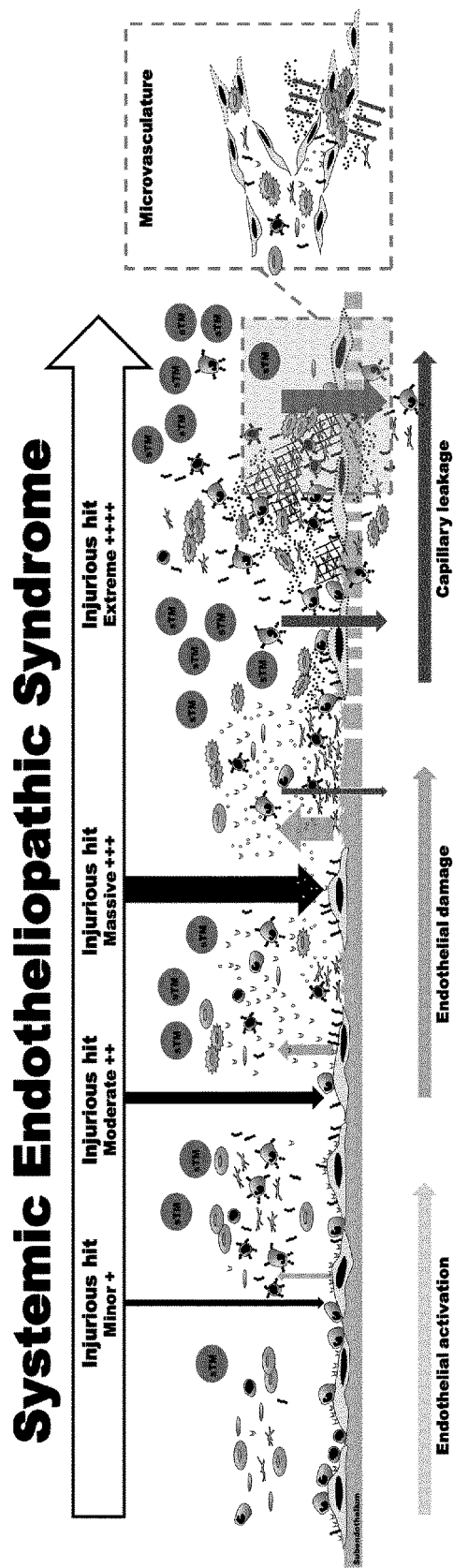
Figure 2A:
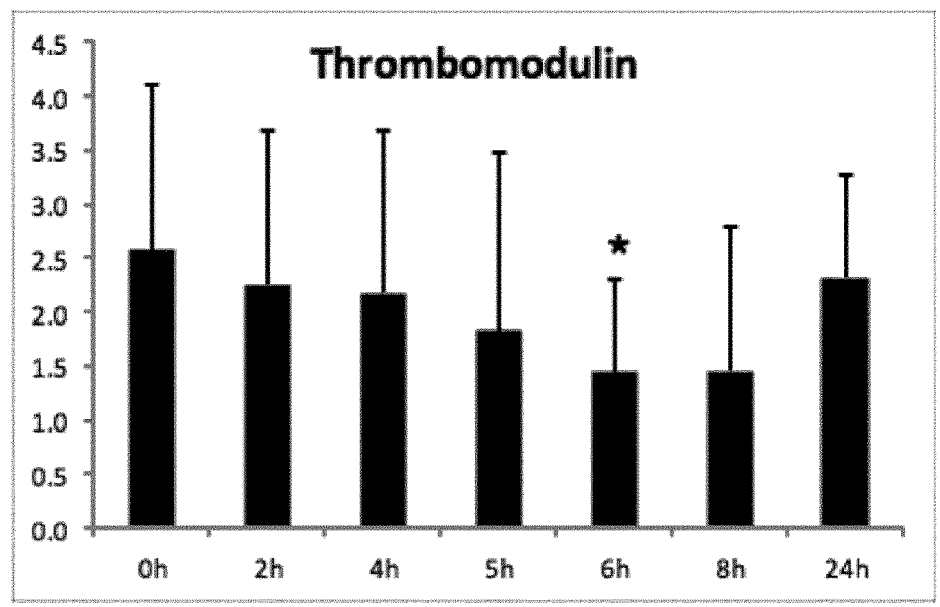
FIGS. 2a-2d are graphs showing test results that illustrate the effect of Flolan® infusion in healthy volunteers.
Figure 2B:
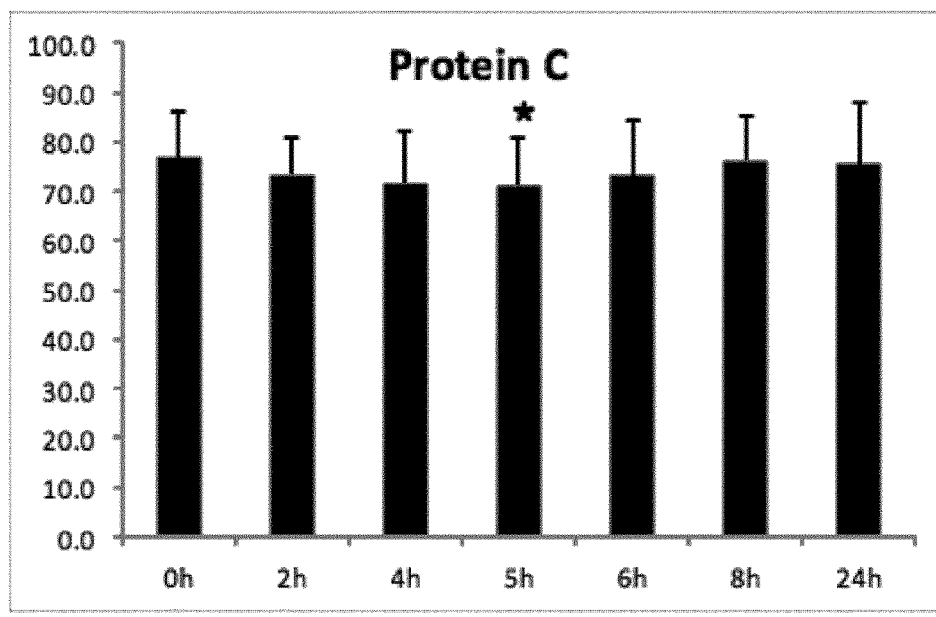
Figure 2C:
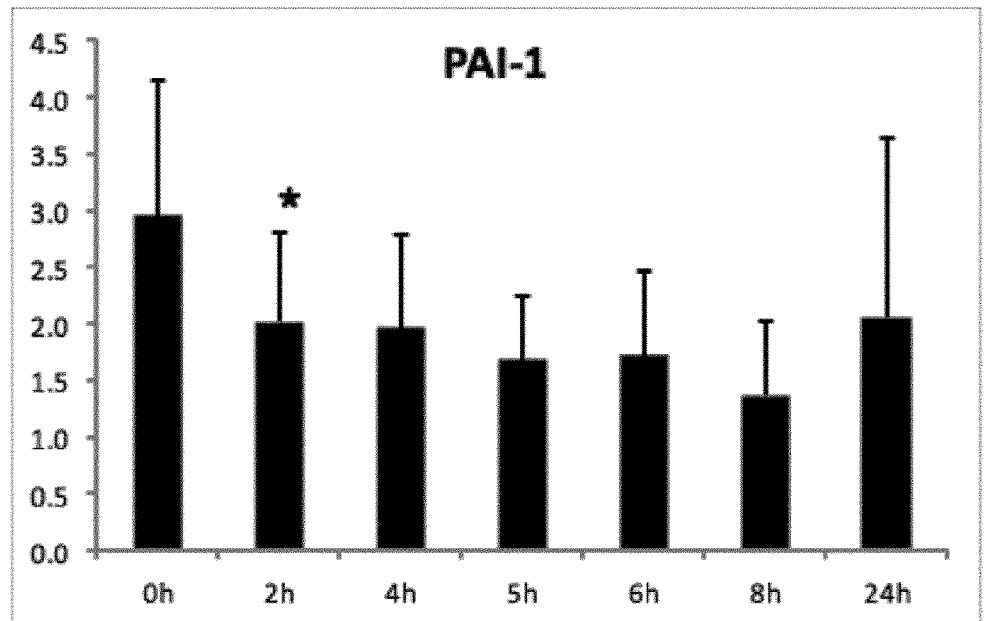
Figure 2D:
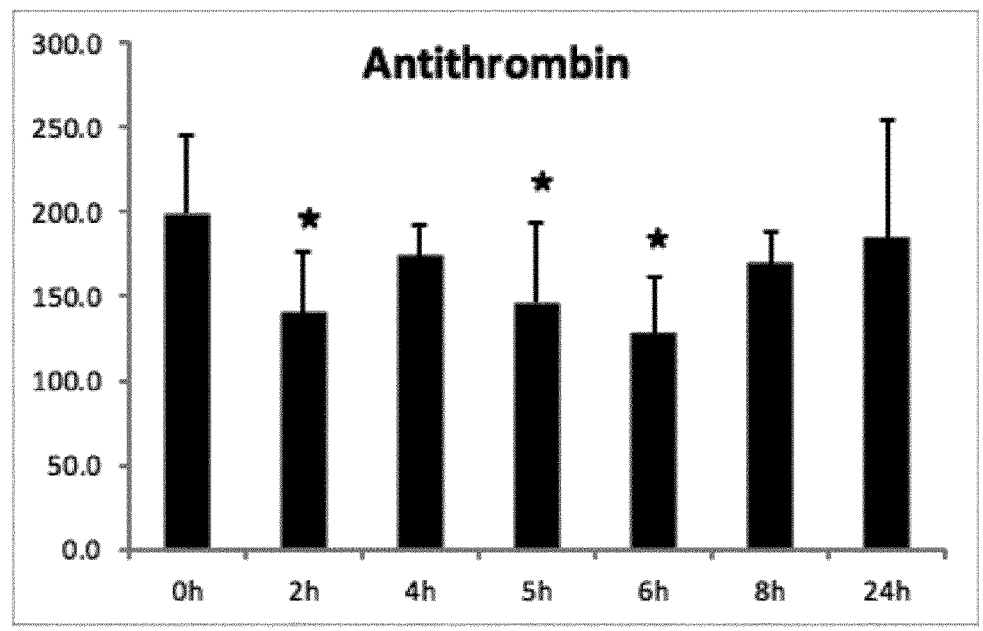

FIG. 1 illustrates at the vascular level how an acute critically ill patient with an increasing injurious hit will experience progressive damage to the endothelium resulting in endothelial shedding/release of thrombomodulin and ensuing increases in circulating soluble thrombomodulin (sTM). Progressive endothelial damage will clinically result in impaired vascular barrier function, capillary leakage, bleeding, hypotension, multiple organ failure and ultimately death. The hypothesized progression of systemic endothelial syndrome is further indicated.

The present disclosure demonstrates that systemic endothelial damage can be identified and diagnosed in a simple manner by using the soluble thrombomodulin level in a blood sample as a biological marker for the presence or absence of systemic endothelial damage. Using thrombomodulin as a biological marker, acute critically ill patients presenting with blood thrombomodulin levels above a given threshold value can be rapidly identified as individuals suffering from systemic endothelial damage; thereby in a simple manner differentiating this group of patients from acute critically ill patients that do not suffer from systemic endothelial damage.

Furthermore, the present disclosure demonstrates that acute critically ill patients diagnosed with systemic endothelial damage can beneficially receive early treatment with compositions comprising prostacyclin or analogues thereof, such as prostacyclin (PGI2) and prostacyclin (PGX) or analogues thereof such as e.g. iloprost, epoprostenol, epoprostenol Sodium, treprostenil sodium, selexipag or beraprost; thereby significantly reducing development of organ failure, improving long term full recovery and reducing mortality.

A central part of the present invention is a personalized medicine approach to treatment i.e., that only acute critically ill patients suffering from systemic endotheliopathic syndrome should be treated with prostacyclin or analogues whereas acute critically ill patients without systemic endotheliopathic syndrome (with low thrombomodulin) should not be treated with prostacyclin or analogues thereof.

Given the direct effects of prostacyclin and analogs thereof on the endothelium (described in details below), the inventors suggest that infusion of low-dose prostacyclin can be used to treat systemic endotheliopathic syndrome.

Proof-of-concept studies of this intervention and its effect on the endothelium measured by changes in circulating levels of thrombomodulin is described below.

The inventors suggest that prostacyclin analogs should be used for treatment of systemic endotheliopathic syndrome, identified in acute critically ill patients by a quick test measuring the level of circulating thrombomodulin.

In further detail the present invention relates to a method of diagnosing, uses of thrombomodulin as a biological marker, a method of treatment; prostacyclin or an analogue thereof for use in novel treatments and compositions comprising prostacyclin or an analogue thereof for use in novel treatments, all according to the embodiments described in this section in particular, and throughout the present disclosure.

In a first aspect and embodiment there is disclosed a method of diagnosing for an individual diagnosed with an acute critical illness, if the individual is a candidate for combination treatment of standard care for the acute critical illness in combination with administration of prostacyclin or an analogue thereof, the method comprising: measuring a baseline concentration of soluble thrombomodulin in blood or plasma of the individual; determining if the baseline concentration of soluble thrombomodulin in blood or plasma is above a threshold level of at least 2.5 ng/ml; and diagnosing the individual as a candidate for combination treatment if the baseline concentration is above the threshold level.

This first aspect and embodiment of the invention is further detailed in FIGS. 7 and 8. In FIG. 7, this first aspect and embodiment relates to items 1 and 2, in FIG. 8 it is illustrated in the column with the heading "Identification".

Generally, the information contained in FIGS. 7 and 8 is identical and the skilled reader will realize that in FIG. 7, as mentioned, items 1 and 2 correspond to the items of FIG. 8 under the heading "Identification", whereas the item 3 of figure corresponds to the items of FIG. 8 under the heading "Treatment", and the items 4 and 5 of FIG. 7 corresponds to the items of FIG. 8 under the heading "Control".

The advantage of presenting the information of FIGS. 7 and 8 in these two corresponding manners will be immediately obvious to the skilled person. In FIG. 7 the emphasis is on the sequential nature of the three main components, "Identification", "Treatment" and "Control", which form the underlying concept of the present invention. However, when the same information is presented as in FIG. 8, it becomes immediately clear to the skilled person that each of these three concepts, identification, treatment, and control, can be individually manipulated within the scope of the disclosed embodiments.

As an example, treatment with prostacyclin or an analog thereof according to the disclosure of the present invention can be initiated immediately upon diagnosis of the patient with an acute critical illness, without hesitating to obtain the further diagnose of systemic endothelial damage through measurement of the patient's thrombomodulin levels. This expedites the initiation of the treatment with prostacyclin or an analogue thereof and is possible due to the low risk of an adverse effect from the mentioned treatment.

When initiating rapid treatment as described above, the first measurement for identification of systemic endothelial damage following the disclosure of the present invention, the also becomes the first control measurement, since a patient which is not in need of prostacyclin treatment can be stopped from receiving further treatment once the first test results have been obtained.

EXAMPLES

Studies of the Endothelium in Acute Critically Ill Patients

The inventors have investigated more than 4,400 patients suffering from severe trauma, sepsis, acute myocardial infarction, resuscitated cardiac arrest and major surgery, including 1,750 patients with varying degrees of sepsis. In these studies, the inventors found that a common and critical link may exist between the severity of the injuries; development of coagulopathy and progressive endothelial damage (endotheliopathy) and mortality.

In the above studies, across the different patient groups, the inventors found that endothelial cellular damage, evidenced by high circulating levels of soluble thrombomodulin, was the strongest marker for mortality.

Importantly, across the investigated groups of different patients with acute critical illness, not all patients developed systemic endotheliopathic syndrome and these patients, with low circulating thrombomodulin, had an excellent outcome with high survival rates. This caused the inventors to realize that in some instances systemic endotheliopathic syndrome may result from acute critical illness such as e.g. severe trauma, sepsis, acute myocardial infarction, resuscitated cardiac arrest and major surgery or other types of acute critical illness, but that this outcome is not necessarily given.

Consequently, patients presenting with concurrent acute critical illness AND high circulating thrombomodulin levels above a given critical threshold limit can be diagnosed as presenting with systemic endotheliopathic syndrome.

To the surprise of the inventors they have now further discovered that patients presenting with systemic endotheliopathic syndrome, i.e. presenting with an acute critical illness and high (above a given threshold) thrombomodulin levels in the blood, will benefit from treatment with prostacyclin or analogues thereof with the aim of curing or alleviating the suffered acute critical illness and reducing patient mortality in situations where patients presenting with the same acute critical illness but not presenting with the additional diagnose of systemic endothelial damage as evidence by a high (above a given threshold) thrombomodulin level in the blood, will not.

Many acute critically ill patients are in shock i.e. a medical emergency condition in which the tissue and organs of the body are deprived of oxygen due to inadequate blood flow.

There are four stages of shock: Initial, compensatory, progressive and refractory. In the initial stage, hypoperfusion causes hypoxia which is followed by compensatory physiological mechanisms, including neural (including sympathoadrenal activation) and hormonal mechanisms in an attempt to reverse the condition. If the condition is not reversed it will proceed into the progressive stage where the compensatory mechanisms begin to fail resulting in severely reduced cell, tissue and organ perfusion and a rise in anaerobic metabolism. Eventually this will lead to leakage of fluid and protein into tissues and upon loss of this (intravascular) fluid, the blood concentration and viscosity will increase, causing sludging of the microcirculation. Also, the prolonged vasoconstriction will cause the vital organs to be compromised due to reduced perfusion. In the final refractory stage, the vital organs will have failed and the shock can no longer be reversed.

All stages of shock are associated with systemic endothelial perturbations ranging from reversible activation and damage to irreversible extensive injury. Therefore the present inventors have realized that administration of prostacyclin or an analogue thereof to acute critically ill patients according to the teaching of the present disclosure, will serve through its beneficial effects on the vascular endothelium and its cytoprotective effects, as an anti-shock therapy.

Testing and Treatment
Acute Critically Ill Patients

Patients that are acute critically ill suffer from e.g. severe trauma, including burn injury, severe infection including sepsis and septic shock, acute myocardial infarction, resuscitated cardiac arrest, major surgery and other conditions that happens immediately and require organ supportive care to survive i.e. ventilator therapy, continuous fluid infusion or blood transfusion, vasopressor therapy etc.

When an acute critically ill patient requires pre-hospital emergency care OR is admitted to the Hospital (the Emergency Department, the Trauma Center or other Departments that have the initial contact with the patient) OR when a hospitalized patient becomes acute critically ill in-hospital (in hospital cardiac arrest (IHCA), in hospital sudden development of septic shock etc.), a blood sample for measurement of thrombomodulin is drawn as early as possible i.e., during transportation of the patient to the Hospital or within minutes up to hours from Hospital admission or in-hospital recognition of the acute critical illness. At the same time point the patient receives standard care for the acute critical illness i.e. ventilation, fluid therapy, blood transfusion, antibiotics, vasopressor therapy, damage control surgery, specific drugs used for the specific acute critical illness e.g. platelet inhibitors and anticoagulants in cardiac arrest caused by myocardial infarction.

Optimally, the patient blood sample is drawn within the first minutes or hours pre-hospital or within the first minutes or hours after admission/recognition of acute critical illness. However, blood samples taken up to 12 hours of admission/recognition of acute critical illness can still be relevant.

Thrombomodulin Testing

The whole blood sample is immediately spun in a centrifuge (e.g. 3000 rpm for 10 minutes) to separate the plasma phase from the blood cell phase. A small volume of the plasma fraction (e.g. from 10-200 µl) is pipetted onto an immunoassay e.g. an enzyme linked immunosorbent assay (ELISA). Currently available ELISA assays require approximately 1 h incubation with patient sample, hereafter 30 min incubation with detection reagent and hereafter 15 min incubation with substrate solution before the ELISA plate can be read by an ELISA reader, corresponding to a total assay time of less than 2 hours. The thrombomodulin concentration in the patient sample is calculated by comparing the assay output e.g. absorbance in the sample to reference samples with a known concentration of thrombomodulin (a standard curve).

When the concentration of thrombomodulin in the patient plasma sample has been determined, this will either be above or below the predetermined threshold level of at least 2.5 ng/ml, preferably 4 ng/ml.

Patients with thrombomodulin values above the threshold level suffer from systemic endotheliopathic syndrome and are candidates for treatment with prostacyclin and analogues thereof.

Patients with thrombomodulin values below the threshold level do not have systemic endothelial damage and will not be candidates for treatment with prostacyclin and analogues thereof.

Preferably, the thrombomodulin test is be a quick point-of-care (POC) test based on whole blood input so a drop of whole blood is placed onto e.g. a lateral flow assay (stick) or another immunoassay platform like e.g. cartridges based on microfluidics technology, to display a result within 2-5 minutes reporting whether a patient has a thrombomodulin level above or below a predetermined threshold level.

Treatment Initiation

Immediately after the test result is available i.e., from minutes to approximately 2-3 hours after blood sampling pre-hospital or patient admission/recognition of acute critical illness when using the ELISA assay described above or 15-30 min after blood sampling pre-hospital or patient admission/recognition of acute critical illness if using the quick whole blood test or POC assay as described above, the patient starts treatment with an intravenous infusion of prostacyclin or analogues thereof in a dose of 0.5-4 ng/kg/min, preferably 1-2 ng/kg/min.

To administer the treatment through an intravenous infusion system, the prostacyclin or analogues thereof either has to be diluted in an appropriate infusion media (e.g. 0.9% saline) to obtain an appropriate concentration of prostacyclin and analogues thereof in the infusion fluid or the prostacyclin and analogues thereof are available in a ready-to-use appropriate infusion solution.

An appropriate amount of prostacyclin and analogues thereof diluted in the intravenous infusion fluid corresponds to a 24-30 hour weight adjusted dose in a small volume, e.g., 100-500 ml. For example, in a patient with a body weight of 70 kg treated for 24 hours with 1 ng/kg/min prostacyclin and analogues thereof as a 4 ml/hour intravenous infusion, this corresponds to a concentration of prostacyclin and analogues thereof of 105 µg/100 ml in the infusion dilution bag (1 ng/kg/min*70 kg*60 min*25 hours=105,000 ng/100 ml=105 µg/100 ml).

For each 24 hours, a new infusion dilution of prostacyclin and analogues thereof will be prepared and administered (as described above) as continues intravenous infusion to the patient for the following 24 hours.

The treating staff (pre-hospital emergency staff, medical doctors, nurses etc.) has simple instructions for how to prepare an appropriate infusion dilution of the treatment for a patient with a given weight. The instructions should be flexible so the treating staff can either administer the treatment as a fixed volume infusion (with variable concentration of prostacyclin and analogues thereof in the infusion fluid, adjusted to patient weight) or a variable volume infusion (with a fixed concentration of prostacyclin and analogues thereof in the infusion fluid), depending on the type of infusion the treating staff normally use pre-hospital or in their Department/ICU/ward.

During the treatment with prostacyclin and analogues thereof the patient receives normal standard of care i.e., supportive care e.g. ventilation, fluid therapy, blood transfusion, antibiotics, vasopressor therapy, damage control surgery, specific drugs used for the specific acute critical illness etc. The therapy is thus an add-on to the normal standard of care treatment regimen.

Optimally the intravenous infusion with prostacyclin or analogues thereof in the dose should begin as early as possible after the thrombomodulin test results has become available i.e., within 30 min-12 hours after known test results, pre-hospital as well as in-hospital. The time to test should not exceed 6 hours after presentation.

Monitoring Treatment Response and Deciding Length of Treatment

The intravenous infusion with prostacyclin and analogues thereof should continue for a minimum of 72 hours (3 days) up till several weeks.

After the first 3 treatment days, the circulating thrombomodulin level should be measured to reveal whether this has decreased, increased or has remained unchanged compared to the baseline (pre-treatment) value. If the thrombomodulin level has decreased from baseline (e.g. a drop of 10% or preferably by 20% or more) and the patient has improved clinically judged by the attending physician (e.g., reduced need for supportive care), the intravenous infusion with prostacyclin and analogues thereof can be ceased so the patient receives just standard care. If however the thrombomodulin level has increased (>10% increase) or remained unchanged from baseline or the patient has not improved clinically judged by the attending physician (e.g., increased need for supportive care), the intravenous infusion with prostacyclin and analogues should continue for the next 24 hours as an add-on to standard care.

After another 24 hours treatment (total 4 treatment days), the circulating thrombomodulin level should be measured to reveal whether this has decreased, increased or has remained unchanged compared to the baseline (pre-treatment) value. If the thrombomodulin level has decreased from baseline (by the aforementioned >10% drop or, preferably, by the aforementioned >20% drop) and the patient has improved clinically judged by the attending physician (e.g., reduced need for supportive care), the intravenous infusion with prostacyclin and analogues thereof can be ceased. If however the thrombomodulin level has increased (>10% increase) or remained unchanged from baseline or the patient has not improved clinically judged by the attending physician (e.g., increased need for supportive care), the intravenous infusion with prostacyclin and analogues should continue for the next 24 hours as an add-on to standard care.

This loop of thrombomodulin guided prostacyclin treatment continues for up till several weeks, or until the patient has recovered clinically to an extend that allows discharge from ICU or receives an stop-resuscitation-code or dies.

After the last 24 hours treatment (until a total of treatment time of up till several weeks), the intravenous infusion with prostacyclin and analogues thereof is ceased.

During the treatment with prostacyclin and analogues thereof, the patient receives standard of care.

Optimally, thrombomodulin values should be measured on a daily basis to decide if the treatment should continue for another 24 hours or should cease.

Example 1—Evidence of Mechanistic Link

A mechanistic link between systemic endotheliopathic syndrome and mortality in acute critically ill patients was first indicated to the inventors in a study of ~1,200 septic patients who were followed daily with blood samples from intensive care unit (ICU) admission and the following four days. Here, the inventors observed that patients who had a reduction in their levels of soluble thrombomodulin (a recognized crude marker of endothelial cell damage) over that time had an increased survival rate compared to patients with stable or increasing levels of thrombomodulin as an indicator of continued endothelial damage. Similarly, the inventors found that patients suffering from severe infection (from local infection to septic shock), trauma, acute myocardial infarction or resuscitated cardiac arrest all present with the same type of systemic endothelial damage, and across all patients the inventors found that thrombomodulin is the strongest marker for mortality.

Together this supports the new notion relevant for the present disclosure that various types of acute critically ill patients may develop the same disease, systemic endotheliopathic syndrome, which can be diagnosed by clinical determination of an acute critical illness and high levels of circulating soluble thrombomodulin Evidence for Medical Use of Prostacyclin and Analogues Thereof for Treatment of Systemic Endotheliopathic Syndrome The inventors have investigated the anti-thrombotic potential of prostacyclin with functional whole blood hemostatic assays proven to correlate with clinical bleeding conditions and transfusion requirements (thrombelastography (TEG) and impedance aggregometry (Multiplate)) and surprisingly they discovered that low-dose prostacyclin infusion had no measurable anti-thrombotic effects.

The inventors investigated (WO 2013/143548, examples 2 and 3) healthy volunteers and acute critical illness and found that in healthy volunteers, 1-4 ng/kg/min prostacyclin infusion neither influenced clot formation nor platelet aggregation. Furthermore, in acute critically ill patients undergoing major abdominal surgery (Example 6) undergoing PCI after acute myocardial infarction [Holmvang et al 2012, Example 5], 0.5-1 ng/kg/min prostacyclin infusion neither influenced clot formation nor platelet aggregation.

Importantly, the inventors surprisingly found that intra- and post-operative prostacyclin infusion was associated with improved clot formation in patients undergoing major abdominal surgery (Example 6). The finding that low-dose prostacyclin infusion (0.5-1 ng/kg/min) in acute critically ill patients does not compromise hemostasis or induce bleeding or adverse events related to impaired hemostasis is in accordance with several other studies of acute critically ill patients treated for hours-to-days with low-dose (0.5-4 ng/kg/min) prostacyclin infusion: Traumatic brain injury patients (0.5-2 ng/kg/min for up to 72 hours) [Grande et al 2000; Naredi et al 2001], liver transplantation patients (4 ng/kg/min for 6 days and 1 ng/kg/min for 7 days, respectively) [Barthel et al 2012; Neumann et al 1999], CABG patients (2 ng/kg/min for up to 48 hours) [Morgera et al 2002], patients with septic shock (1 ng/kg/min for 24 h and a dose increasing cardiac index 15% (1-2 ng/kg/min) for several hours, respectively) [Kiefer et al 2001; Lehmann et al 2000], patients undergoing surgery for acute lower limp ischemia (0.5-2 ng/kg/min for 6 hours/day for 4-7 days) [de D G et al 2006; de D G et al 2007] and patients undergoing elective open repair of abdominal aortic aneurysm (0.8-1.2 ng/kg/min for 72 h) [Beirne et al 2008].

In conclusion it has now been found that prostacyclin dose-dependently inhibits platelet aggregation but low-dose prostacyclin infusion (up to 4 ng/kg/min) but does not compromise hemostasis or induce bleeding or adverse events related to impaired hemostasis in healthy volunteers and acute critically ill patients.

Example 2—Reevaluation of a Prior Art Study

Healthy Volunteer Study: Safety and Efficacy of 4 Ng/Kg/Min i.v. Flolan® Infusion in Healthy Subjects, Reported in WO 2013/143548.

The study was conducted investigating the influence of 2 hours i.v. Flolan® (epoprostenol sodium, prostacyclin analog) infusion at a dose of 4 ng/kg/min in eight healthy male volunteers.

Endothelial function was evaluated in the study e.g. by measuring plasma levels of endothelial derived biomarkers by commercially available ELISA kits. Biomarkers indicating: Endothelial glycocalyx damage (syndecan-1), endothelial cell damage (thrombomodulin) or necrosis (nucleosomes, HMGB1), endothelial cell activation (PAI-1) and endothelial cell anticoagulation (protein C, antithrombin) were investigated (FIG. 2).

Prostacyclin in the administered dose did not change blood pressure or heart rate from baseline values at any time point during the study period. Furthermore, no changes were observed in Multiplate and TEG values comparing baseline and later values, indicating that 4 ng/kg/min i.v. prostacyclin infusion does not influence hemodynamics or hemostasis.

The administered dose of prostacyclin was observed to have an endothelial protective effect evidenced by a marked decrease in the circulating level of thrombomodulin, an effect that appeared to be prolonged continuing for several hours after ceasing the prostacyclin infusion. Also, the circulating level of protein C decreased in the hours after ceasing the prostacyclin infusion, indicating that prostacyclin enhanced activation of protein C. The circulating level of PAI-1, an inhibitor of fibrinolysis shed from the activated endothelium, also declined further indicating that the prostacyclin infusion deactivated the endothelium and enhanced endogenous fibrinolysis. Finally, the circulating level of antithrombin decreased indicating that a higher amount of antithrombin was attached to the endothelial glycocalyx rather than being circulating in its soluble form i.e. providing the endothelium with improved anticoagulant properties.

The finding that the administered dose of prostacyclin was associated with concurrent decreases in circulating thrombomodulin, protein C, PAI-1 and antithrombin in healthy individuals is reported here as a proof-of-concept of the endothelial protective effect of prostacyclin of importance for its capacity to treat systemic endotheliopathic syndrome.

Conclusion:

In this study the inventors found that i.v. infusion of a prostacyclin analog at a dose applied widely clinically (4 ng/kg/min) neither influenced hemodynamics nor whole blood hemostatic competence. The finding that the prostacyclin analog protected the endothelium supports the notion, that administration of low-dose prostacyclin or prostacyclin analogs, in particular iv-administration, is useful for treatment of systemic endotheliopathic syndrome.

Example 3—Reevaluation of a Prior Art Study

Healthy Volunteer Study: Efficacy of 1 ng/kg/Min i.v. Ilomedin® Infusion in Healthy Subjects. Reported in WO 2013/143548.

A study was reported investigating the influence of 2 hours i.v. Ilomedin® (iloprost, prostacyclin analog) infusion at a dose of 1 ng/kg/min in eight healthy male volunteers. Blood samples for endothelial function were collected at the following time-points: Before the infusion (0 h), after 30 min infusion (30 min), immediately after ceasing the infusion (2 h) and 2 hours after the end of iloprost infusion.

Figure 3A:
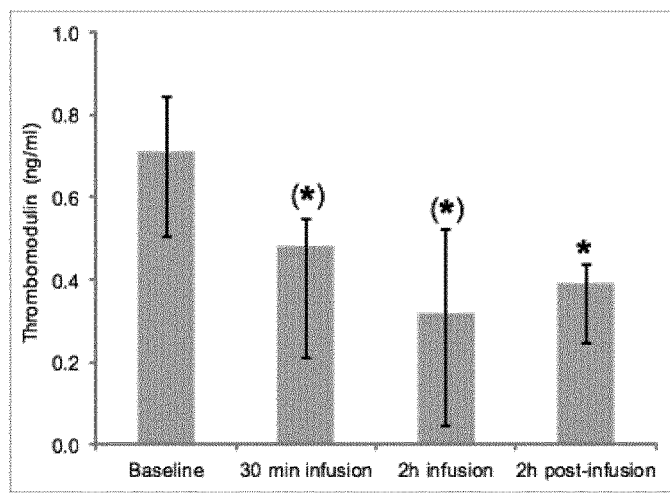
FIGS. 3a to 3c are graphs showing test results that illustrate the effect of Ilomedin® infusion in healthy volunteers.
Figure 3B:
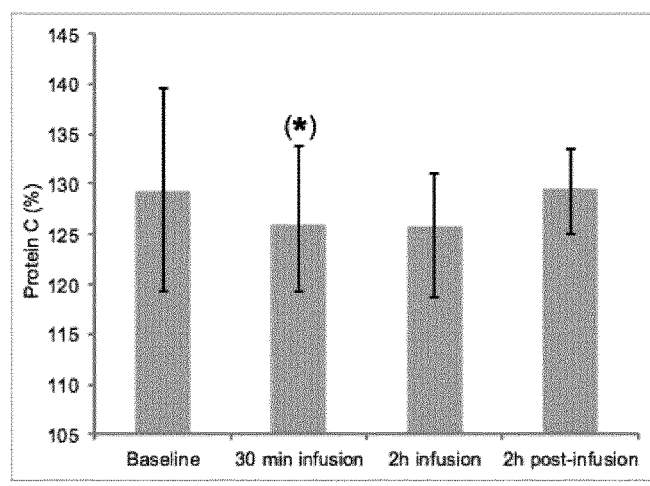
Figure 3C:
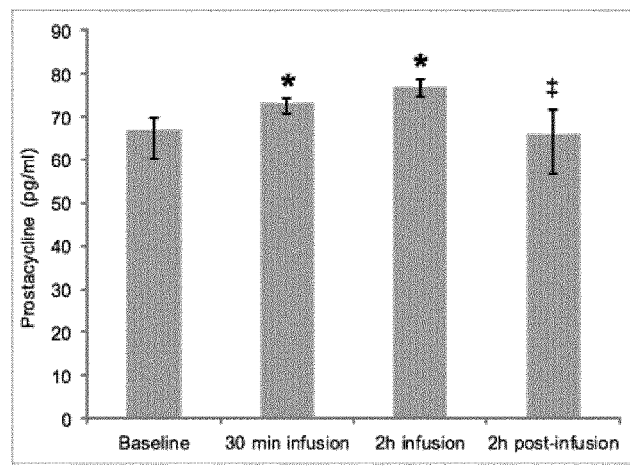

Endothelial function was evaluated by measuring plasma levels of endothelial derived biomarkers by commercially available ELISA kits. Biomarkers indicating: Endothelial glycocalyx damage (syndecan-1), endothelial cell damage (thrombomodulin) and endothelial cell anticoagulation (protein C) were investigated. Furthermore, we measured plasma concentration of prostacyclin (FIG. 3).

The administered dose of iloprost had an endothelial protective effect evidenced by a marked decrease in the circulating level of thrombomodulin, an effect that appeared to be prolonged continuing for several hours after ceasing the iloprost infusion. Also, the circulating levels of protein C and Syndecan-1, the latter a biomarker of glycocalyx damage, decreased during iloprost infusion, indicating that prostacyclin enhanced activation of protein C (resulting in a decline in the non-activated form of protein C) and protected the glycocalyx. Finally, the circulating level of prostacyclin increased approximately 15% during iloprost infusion confirming that systemically detectable increases in prostacyclin were obtained by low-dose 1 ng/kg/min iloprost infusion.

Conclusion:

This study support the notion that an endothelial protective effect of low-dose i.v. infusion with a prostacyclin analog (1 ng/kg/min, iloprost, Ilomedin®) supporting the capacity of administration of low-dose prostacyclin or prostacyclin analogs, in particular iv-administration, for treatment of systemic endotheliopathic syndrome.

Example 4—Revaluation of Prior Art

Patient Study: Safety and Efficacy of Pre-Filter Flolan® Infusion in Critically Ill Patients [Windelov et al 2010]

Furthermore, in a retrospective study of intensive care patients needing continuous renal replacement therapy, the inventors found that patients who received prostacyclin in the dialysis filter had lower 30-day mortality compared to patients who received heparin in the filter as an anticoagulant (21% vs. 39%)

The inventors conducted a retrospective study of critically ill patients treated or not treated with prostacyclin infusion during their intensive care unit (ICU) stay [Windelov et al 2010]. Ninety-four critically ill patients admitted to the ICU for medical or surgical complications, underwent hemofiltration (continuous renal replacement therapy, CRRT) with or without concomitant Flolan® (epoprostenol sodium, prostacyclin analog) treatment. Flolan® was administered at a low dose (5 ng/kg/min) in the filters to prevent these from clotting and consequently, there was only a minor spill-over of Flolan® to the systemic circulation.

The study revealed that the two groups (prostacyclin vs heparin) were comparable with regard to disease severity (APACHE II score) at ICU admission but during their ICU stay (before CRRT), prostacyclin patients appeared more severely ill evidenced by more patients having septic shock, disseminated intravascular coagulation (DIC), severe thrombocytopenia and a lower platelet count at start of hemofiltration (Table 1).

During CRRT with either prostacyclin or heparin, platelet count increased in the prostacyclin patients whereas it declined in the heparin patients, indicating reduced disease severity in the patients treated with prostacyclin (Table 1). Importantly, when comparing mortality, the prostacyclin patients tended to have decreased mortality at 30 days (21% vs. 39%, p=0.12), 90 days (34% vs. 53%, p=0.10) and 365 days (38% vs. 57%, p=0.09).

Conclusion:

The finding of increased platelet count and reduced mortality in CRRT patients receiving prostacyclin in the filters indicate that the minor spill-over of prostacyclin to the systemic circulating influences the endothelium beneficially in acute critically ill patients by limiting consumption of platelets, microvascular occlusion, organ failure and mortality, i.e. hallmarks of systemic endotheliopathic syndrome.

Example 5—Revaluation of Prior Art

Patient Study: Safety and Efficacy of 0.5 ng/kg/Min i.v. Ilomedin® Infusion in PCI Patients [Holmvang et al 2012]

The inventors conducted a randomized placebo controlled double blind clinical trial investigating safety and efficacy of 24 hours i.v. Ilomedin® (iloprost, prostacyclin analog) infusion at a dose of 0.5 ng/kg/min compared to placebo in 17 patients with acute myocardial infarction (AMI) undergoing percutanuous coronary intervention (PCI) with stent implantation [Holmvang et al 2012]. Patients randomized to 24 hours active (n=9) or placebo (n=8) therapy were evaluated for hemodynamics, bleeding events and for functional whole blood hemostasis (Multiplate, TEG) and endothelial function in blood sampled before iloprost infusion (baseline), during infusion (1 h, 6 h and 24 h) and 24 hours after ceasing iloprost infusion (48 h).

Bleeding was evaluated by GUSTO criteria (severe, moderate, mild, none) and hemostasis was evaluated by Multiplate and TEG according to the manufactures recommendations. Endothelial function was evaluated by measuring plasma levels of endothelial derived biomarkers by commercially available ELISA kits. Biomarkers indicating: Endothelial glycocalyx damage (syndecan-1), endothelial cell damage (thrombomodulin), endothelial cell activation (sE-selectin, ICAM-1) and anticoagulation (protein C) were investigated.

The study revealed that patients in the two groups (iloprost vs placebo) were comparable with regard to baseline demography and disease severity. Furthermore, no differences in hemodynamics, bleeding events, Multiplate or TEG were observed between groups during or after iloprost infusion.

Importantly, the inventors found that sE-selectin, a biomarker reflecting endothelial activation, decreased significantly from baseline to 48 h in the iloprost patients whereas it increased in the placebo patients (FIG. 4) difference between patient groups p=0.008), indicating an endothelial protective effect of iloprost continuing after ceasing iloprost infusion.

Conclusion:

AMI PCI patients treated with 24 hours i.v. prostacyclin infusion displayed evidence of prolonged reduction in endothelial activation continuing 24 hours after ceasing the infusion. The prostacyclin infusion did not negatively influence hemodynamics, bleeding events or hemostasis. This study supports the notion that prolonged low-dose i.v. prostacyclin infusion in acute critically ill patients is safe and effective in protecting the endothelium and hence capable of treating systemic endotheliopathic syndrome.

Example 6—Safety and Efficacy of 1 ng/kg/Min i.v.

Patient Study: Safety and Efficacy of 1 ng/kg/Min i.v. Ilomedin® Infusion in Whipple (Major Abdominal Surgery) Patients The inventors conducted a randomized placebo controlled double blind clinical trial investigating safety and efficacy of intra- and post-operative i.v. Ilomedin® (iloprost, prostacyclin analog) infusion at a dose of 1 ng/kg/min compared to placebo in patients undergoing whipple surgery at Rigshospitalet, a tertiary level teaching University hospital in Copenhagen, Denmark. The inclusion criteria were adults (age years) undergoing whipple surgery based on surgical indication due to cancer/dysplasia, familial adenomatous polyposis or inflammation/pancreatitis. However, all included patients had cancer as a surgical indication: C. pancreas n=12; C. papilla vateri n=2; C. ductus choledochus n=1; Cholangiocarcinoma n=1. The patients were randomized to receive i.v. infusion with iloprost (1 ng/kg/min, active treatment, n=8) or saline (0.9%, placebo treatment, n=8) at an equal volume during surgery (intra-operative: median ~5 hours) and 6 hours after surgery (post-operative), yielding a total active/placebo infusion time of ~11 hours.

Data on demography, co-morbidities, surgical time and 28-day mortality were assessed. Hemodynamics were measured continuously (heart rate (HR), systolic, diastolic and mean arterial pressure (SBT, DBT, MAP)) or at baseline, end of surgery and 6 h and 24 h post-operative (systemic vascular resistance (SVR), stroke volume (SV), central venous pressure (CVP)). The volume and number of units of red blood cells (RBC), plasma and platelet concentrates administered were recorded at the end of surgery, 6 h and 24 h post-operative. Bleeding volume was assessed intra-operative and 6 h and 24 h post-operative. The volume of crystalloids and colloids (only albumin was allowed) was, together with urine output, recorded intra-operative and 6 h and 24 h post-operative.

Blood samples for evaluation of functional whole blood hemostasis (TEG) and endothelial function were collected pre-commencing infusion with study drug (baseline), at the end of surgery (post-op) and 6 h after surgery just before ceasing study drug infusion (6 h). Blood samples for routine biochemistry (hemoglobin, creatinine and lactate) were collected at baseline, post-op and 6 h and 24 h post-operative.

TEG was performed according to the manufactures recommendations. Endothelial function was evaluated by measuring plasma levels of endothelial derived biomarkers by commercially available ELISA kits. Biomarkers indicating: Endothelial glycocalyx damage (syndecan-1), endothelial cell damage (thrombomodulin) and necrosis (nucleosomes) were investigated.

Comparing iloprost and placebo patients, no differences were found with regard to demography, comorbidities, surgical indication or 28-day mortality. Furthermore, the groups received a similar volume of fluids intra- and post-operative and displayed comparable changes in hemodynamics.

However, with regard to transfusion requirements, hemostasis and endothelial function, the inventors surprisingly found major differences between the treatment groups as iloprost patients had reduced RBC transfusion requirements, reduced increases in lactate, improved functional hemostasis and reduced endothelial damage (FIG. 5abc).

Thus, in brief, placebo patients received more intra- and post-operative RBC compared to iloprost patients (median 0 ml (IQR 0-163) vs. 695 ml (IQR 0-969), p=0.083) and a significantly larger volume of RBC from arrival at the post-operative ward and 6 h post-operatively (iloprost patients 0 ml (IQR 0-0) vs. placebo patients 115 ml (IQR 0-296), p=0.027). Furthermore, placebo patients tended to have lower post-operative hemoglobin compared to iloprost patients (median 6.2 mmol/l (IQR 5.9-6.4) vs. 6.7 mmol/l (IQR 6.5-7.7), p=0.058) and post-operatively lactate increased in placebo patients but remained unchanged in iloprost patients indicating that iloprost infusion improved microvascular perfusion. Considering hemostatic competence, placebo patients displayed impaired intra-operative hemostatic competence as TEG maximum clot firmness decreased intra-operatively in placebo patients (p=0.034) whereas it remained stable in iloprost patients (p=NS).

Importantly, the inventors found that iloprost patients displayed evidence of improved endothelial protection and reduced endothelial damage compared to placebo patients (FIG. 5abc) as thrombomodulin and nucleosome levels, markers of endothelial cell damage and necrosis, increased significantly more intra- and postoperatively in placebo patients compared to iloprost patients (FIG. 5ab). Also, the inventors observed a trend towards higher levels of syndecan-1 in placebo patients compared to iloprost patients (FIG. 5c) indicating that iloprost protected the glycocalyx.

Together these findings indicate that iloprost infusion exerted an endothelial protective effect in acute critically ill surgical patients.

Conclusion:

Whipple patients treated with iloprost infusion intra- and post-operatively received fewer RBC transfusions, had improved hemostatic capacity, improved microvascular perfusion and evidence of reduced endothelial damage together supporting a capacity of prostacyclin infusion to treat systemic endotheliopathic syndrome.

Example 7—Revaluation of Prior Art

The inventors have measured soluble thrombomodulin levels in blood plasma from 2,118 acute critically ill patients suffering from trauma, myocardial infarction, cardiac arrest, sepsis, severe sepsis and septic shock (Table 2). The blood sample for thrombomodulin measurement was taken immediately upon admission to the hospital or immediately after observation of the occurrence of the acute critical illness.

The inventors discovered that the acute critically ill patients could be stratified into a group with low mortality rate and a group with high mortality rate based on the measured thrombomodulin level. Thus, a high level of thrombomodulin in blood plasma was associated with high 28-day mortality whereas a low thrombomodulin level in blood plasma was associated with low 28-day mortality.

Table 2 details a study of median thrombomodulin levels in plasma/serum (ng/ml) in 2,118 acute critically ill patients suffering from trauma, myocardial infarction, resuscitated cardiac arrest, sepsis, severe sepsis or septic shock, stratified according to gender and 28-day outcome (survival vs. mortality).

The inventors discovered that there was a significant difference in thrombomodulin levels between survivors and non-survivors across all diseases (p<0.0001), but no difference in thrombomodulin between male and female (p=0.114).

FIG. 6 displays the receiver operating characteristic (ROC) curve of thrombomodulin for predicting 28-day mortality in acute critically ill patients suffering from trauma, myocardial infarction, cardiac arrest, sepsis/severe sepsis/septic shock. Soluble thrombomodulin level area under the curve (AUC) for predicting 28-day mortality is 0.744 (0.712-0.776), p<0.0001, with the highest Youden Index revealing a threshold level of 4.0 ng/ml thrombomodulin in blood plasma. At the 4 ng/ml threshold level, sensitivity is 0.781 and 1-specificity is 0.407 of the test for prediction of 28-day mortality. Based on these data, 85% of the patients whom die before 28 days have thrombomodulin>4 ng/ml.

Based on the inventors data, choosing a lower threshold level of thrombomodulin results in increased true-positive rate (sensitivity) and increased false-positive rate (1-specificity) whereas choosing a higher threshold level of thrombomodulin results in reduced true-positive rate (sensitivity) and reduced false-positive rate (1-specificity) (Table 3). Consequently, both a lower and higher threshold level of thrombomodulin will result in a lower Youden Index and hence lower performance of the diagnostic test.

It should be noted that a thrombomodulin level of 4 ng/ml in plasma cannot be expected to be identical to the thrombomodulin level measured in whole blood since the plasma fraction of whole blood is only approximately 55%. (Discussed below based on data comparing the thrombomodulin level in plasma and whole blood).

Conclusion:

Acute critically ill patients with blood or blood plasma thrombomodulin values above 4 ng/ml suffer from systemic endotheliopathic syndrome and will benefit from treatment with prostacyclin or analogs thereof.

Due, however, to the observed benefits of the present invention; the inventors suggest to operatively use a lower threshold level than 4 ng/ml (plasma/serum) as an indicator for treatment with prostacyclin or an analogue thereof according to the present invention. A threshold level corresponding to a plasma/serum level of 2.5 ng/ml is considered satisfactory in the method of the invention or values in between 2.5 ng/ml to 4 ng/ml, such as e.g. 3.0 or 3.5 ng/ml thrombomodulin in plasma/serum.

Selecting e.g. a threshold level of 2.5 ng/ml will result in an almost 91% capture of treatment suited subjects (true positive), however at the cost of a larger number of patients being unnecessarily treated with prostacyclin or an analogue thereof (false positive). Due to the high safety profile and low risk of adverse effects in treatments using the suggested low-dose prostacyclin or analogues thereof, it seems reasonable to proceed in such a manner, in particular since later control according to the invention will limit the unnecessary treatment exposure received by patients not in need thereof.

Example 8—Trauma

Table 4a details results based on 635 trauma patients. It was found that the level of sTM (soluble thrombomodulin) at admission in trauma patients depended on injury severity (increases most in patients with high abbreviated injury severity score (AIS) for abdomen and thorax i.e., severe abdominal and thorax injuries) including shock degree reflecting that the proportion of patients with sTM above 2.5 ng/ml differ between cohorts of severely (84.9%) and moderately (45.2%) injured patients (Table 4a).

Table 4b details results based on 270 trauma patients. It was found that in the first 24 h and 72 h, the level of sTM increases in 64% and 80% of the moderately injured patients, respectively, and from 24 h to 72 h, sTM increases in 61% of the patients. The absolute and proportional change in sTM from admission and 72 h onward is displayed in Table 4b, ranging from a median increase of 0.31-0.72 ng/ml corresponding to 12-34% increases.

It was Observed that:
The Level of sTM at Baseline and During Follow-Up is Linked to Complications
Mortality When comparing the sTM level in survivors and 28d non-survivors, the sTM level at admission (median IQR) (2.95 ng/ml (1.73-4.21) vs. 2.29 ng/ml (1.44-3.38)), at 24 h (3.92 ng/ml (3.7-5.55) vs. 2.94 ng/ml (2.2-4.32)) and 72 h (4.56 ng/ml (3.95-5.85) vs. 3.35 ng/ml (2.67-4.6)) is higher in non-survivors compared to survivors (p=0.047, p=0.016 and p=0.076, respectively).

Sepsis

High sTM level at admission tend to be associated with increased risk of sepsis the first 28d (ROC for admission sTM on development of sepsis within 28d is AUC 0.594 (95% CI 0.487-0.700), p=0.085).

Renal Replacement Therapy (RRT) (Single Organ Failure)

sTM levels at 24 h and 72 h tend to be associated with increased risk of renal replacement therapy (RRT) during the first 28d (ROC for 24 h sTM AUC 0.771 (0.556-0.985), p=0.068 and ROC for 72 h sTM AUC 0.877 (0.789-0.966), p=0.072)) emphasizing that high sTM levels after admission are also linked to organ failure.

The Change in sTM Level from Admission and Onward is Linked to Complications

Bleeding sTM increases from 24-72 h in more patients who experience bleedings within the first 24 h of admission than in patients who do not bleed the initial 24 h (76% vs. 50% display sTM increases, p=0.063).

Renal Replacement Therapy (RRT) (Single Organ Failure)

sTM increases from 0-24 h, from 0-72 h and from 24-72 h in all (100%) patients who during the first 28 days require RRT due to development of kidney failure (single organ failure). Furthermore, an increase in sTM the initial 24 h from admission (0-24 h) is associated with increased risk of RRT (ROC for sTM change 0-24 h on RRT within 28d is 0.794 (0.619-0.969), p=0.048). Also, the change in sTM from 0-24 h is positively correlated with RRT days (kidney failure) (both p<0.05) emphasizing that increases in sTM the first 24 h from admission is associated with enhanced development of organ failure.

Ventilation (Single Organ Failure)

Also, the change in sTM from 0-24 h is positively correlated with ventilator days (length of ventilator treatment i.e., respiratory failure) emphasizing that increases in sTM the first 24 h from admission is associated with enhanced development of organ failure.

Disease severity scores for trauma were: Injury Severity Score (ISS) [evaluated at admission], Glasgow Coma Scale (GCS) score [evaluated at admission], and Sequential Organ Failure Assessment (SOFA) score [evaluated daily in the ICU].

Together, these findings indicate that early and continued measurement of blood or plasma thrombomodulin levels in trauma patients will allow identification of high-risk patients i.e., patients with systemic endothelial damage and thus patients with the highest thrombomodulin levels or highest increases in thrombomodulin. High-risk patients with high thrombomodulin levels due to systemic endothelial damage will benefit from therapy with low-dose prostacyclin or analogs thereof, which will be safe even in trauma patients due to the low-dose regimen.

Example 9—Cardiac Arrest

Based on n=169 patients resuscitated from cardiac arrest. It was found that the level of sTM at admission in resuscitated cardiac arrest patients depends on the time in shock and the depth of shock (higher sTM with longer time from CA to ROSC and with lower pH and higher lactate), the catecholamine level (higher sTM with higher adrenaline dose administered) and the age of the patient (higher sTM in older patients).

Table 5a details the proportion of OHCA patients with sTM>2.5-5-5 ng/ml at admission, 24 h, 48 h and 72 h. In the first 24 h, 48 h and 72 h, the level of sTM increases in 35%, 52% and 43% of the patients compared to baseline and sTM increases in 77% from 24-48 h, in 38% from 24 h-72 h and in 16% from 48 h-72 h. The median absolute changes from 0-24 h, from 0-48 h and from 0-72 h in all patients are 0.27 ng/ml, 1.08 ng/ml and 0.80 ng/ml, respectively.

Table 5b details the absolute and proportional (median) changes in sTM from admission and 24 h and 72 h onward in 28 day survivors and non-survivors. Importantly, the change in sTM in 28d survivors compared to non-survivors differs significantly, with the most pronounced difference being that sTM remains unchanged in survivors the first 24 h whereas it increases 16% in non-survivors.

Table 5c details the predictive value of sTM at different time-points for poor cognitive outcome (CPC/mRS 4) evaluated by ROC analysis. As can be learned from the results continued high sTM levels remain closely linked to high mortality and poor outcome.

It was Observed that:

The Level of sTM at Baseline and During Follow-Up is Linked to Complications

Mortality

When comparing the sTM level in 28d survivors and non-survivors, the sTM levels at admission, 24 h, 48 h and 72 h are all increased in non-survivors compared to survivors: Admission (7.78 ng/ml (6.36-11.41) vs. 6.56 ng/ml (5.17-8.31), p<0.0001), 24 h (9.04 ng/ml (6.28-11.61) vs. 6.6 ng/ml (5.28-9.27), p<0.0001), 48 h (9.96 ng/ml (7.3-12.85) vs. 7.79 ng/ml (6.31-10.52), p<0.006) and 72 h (8.46 ng/ml (5.95-12.16) vs. 7.23 ng/ml (5.46-9.91), p=0.058).

Poor Neurologic Outcome

Also, high sTM level at admission and after 24 h, 48 h and 72 h all predict poor cognitive outcome evaluated by the CPC and mRS scores (Table 5c).

The Change in sTM Level from Admission and Onward is Linked to Complications

The increase in sTM from admission to 24 h, 48 h and 72 h onward all correlate with the time in and depth of shock (time from CA to ROSC, pH and lactate) and the administered adrenaline dose (all p<0.05) emphasizing that the severity of the initial "hit" (shock, catecholamines) drives progressive endothelial damage and hence increases in sTM.

Mortality

The magnitude of the sTM increase from 0-24 h is associated with mortality evidenced by ROC: Higher sTM increase from 0-24 h is associated with increased 28d mortality with AUC 0.587 (0.484-0.689), p=0.103.

Poor Neurologic Outcome

Also, the magnitude of the sTM increase from 0-24 h is associated with cognitive outcome evidenced by ROC: The predictive value of the sTM increase from 0-24 h is associated with CPC 3 (AIC 0.566 (0.469-0.633), p=0.192) and mRS 4 (AUC 0.578 (0.480-0.676), p=0.124) indicating that progressive increases in sTM are associated with poor cognitive outcome.

Disease severity scores for cardiac arrest were: Cerebral Performance Category (CPC), and modified Rankin Scale (mRS) [cardiac arrest].

Together, these findings indicate that early and continued measurement of blood or plasma thrombomodulin levels in patients resuscitated from cardiac arrest will allow identification of high-risk patients i.e., patients with systemic endothelial damage and thus patients with the highest thrombomodulin levels or highest increases in thrombomodulin. High-risk patients with high thrombomodulin levels due to systemic endothelial damage will benefit from therapy with low-dose prostacyclin or analogs thereof, which will be safe in patients resuscitated from cardiac arrest due to the low-dose regimen.

Example 10—Myocardial Infarction

Based on n=571 STEMI patients. It was found that the level of sTM at admission in patients with acute myocardial infarction (ST segment elevation myocardial infarction, STEMI) is linked to disease severity and outcome with higher sTM levels in patients with more severe disease (highest levels in patients with shock and ICU requirement).

Table 6 details the proportion of OHCA patients with sTM>2.5-5-5 ng/ml at ICU admission (data from two different cohorts of septic patients).

It was Observed that:

The Level of sTM at Admission is Linked to Mortality and Complications

Mortality

When comparing the level of sTM at admission in 28-day and 90-day non-survivors and survivors, the 28-day (3.23 ng/ml (2.23-4.16) vs. 2.09 ng/ml (1.56-2.96), p<0.0001) and 90-day (3.23 ng/ml (2.20-4.16) vs. 2.10 ng/ml (1.56-2.96), p<0.0001) non-survivors have higher sTM levels compared to survivors. sTM at admission correlates inversely with days to death (p=0.045) reflecting that high sTM is associated with faster progression to death. By ROC analyses, admission sTM is a strong predictor of 28-day (AUC 0.718 (0.635-0.801), p<0.0001) and 90-day (AUC 0.713 (0.633-0.792), p<0.0001) all cause mortality and of 28-day (AUC 0.736 (0.648-0.824), p<0.0001) and 90-day (AUC 0.726 (0.639-0.812), p<0.0001) cardiovascular disease mortality.

Disease Severity

Admission sTM correlates positively with Troponin I (a biochemical marker for myocardial injury) (p=0.008) by ROC analysis sTM is associated with shock before PCI (AUC 0.580 (0.495-0.666), p=0.061) and with risk of ICU admission (AUC 0.605 (0.510-0.701), p=0.053). Also, sTM is a strong predictor of 28-day (AUC 0.640 (0.555-0.725), p=0.007) and 90-day (AUC 0.644 (0.564-0.724), p<0.0001) congestive heart failure.

Together, these findings indicate that early and continued measurement of blood or plasma thrombomodulin levels in patients with myocardial infarction will allow identification of high-risk patients i.e., patients with systemic endothelial damage and thus patients with the highest thrombomodulin levels or highest increases in thrombomodulin. High-risk patients with high thrombomodulin levels due to systemic endothelial damage will benefit from therapy with low-dose prostacyclin or analogs thereof, which will be safe in myocardial infarction patients due to the low-dose regimen. It is expected that prostacyclin therapy in myocardial infarction patients treated with PCI (percutaneous coronary intervention) will prevent and treat sequelae from the injurious hit such as myocardial infarction with shock, ischemia-reperfusion, catechol-amines etc.

Example 11—Sepsis/Severe Sepsis/Septic Shock

Based on two different cohorts (n=749 and n=184) of patients with sepsis/severe sepsis/septic shock it was observed that the level of sTM at admission in patients with sepsis/severe sepsis/septic shock is closely linked to disease severity with higher sTM levels in patients with higher disease severity scores (APACHE II, SOFA) and hence higher degree of organ dysfunction i.e., higher lactate, lower blood pressure, lower platelet count and hemoglobin, lower urine output, higher BUN and creatinine.

It was Observed that

The Level of sTM at Admission is Linked to Mortality and Complications

Mortality

When comparing the level of admission sTM in 7-day, 28-day and 90-day non-survivors and survivors, sTM is increased in the 7-day (9.21 ng/ml (6.74-12.79) vs. 7.35 ng/ml (4.77-10.35), p=0.001), 28-day (9.34 ng/ml (6.86-12.5) vs. 6.81 ng/ml (4.47-9.66), p<0.0001) and 90-day (9.11 ng/ml (6.31-11.92) vs. 6.66 ng/ml (4.61-9.7), p=0.006) non-survivors compared to survivors.

sTM at admission correlates inversely with days to death (p=0.001) reflecting that high sTM is associated with faster progression to death. By Cox proportional hazards models, the admission sTM level is a strong predictor of 7-day, 28-day and 90-day mortality (all p<0.001) and by ROC analysis, sTM is a strong predictor of mortality: 7-day mortality AUC 0.65 (0.56-0.75), p=0.005; 28-day mortality AUC 0.68 (0.60-0.76), p<0.001 and 90-day mortality AUC 0.63 (0.54-0.71), p=0.004.

Disease Severity Scores sTM at admission correlates strongly positively with SAPS II score (p<0.0001) and SOFA score (p=0.003), and for each 1 ng/ml increase in sTM, SAPS II score increases 1.32 (95% CI 0.73-1.91) (p<0.001) points and SOFA score increases 0.17 (95% CI 0.07-0.27) points (p=0.001).

Bleeding and Transfusion Requirements

The sTM level at admission predicts general bleeding in the ICU (ROC AUC 0.598 (0.498-0.678), p=0.059), serious bleeding (requiring >3 RBC) (ROC AUC 0.612 (0.506-0.717), p=0.068) and upper GI bleeding (ROC AUC 0.680 (0.551-0.809), p=0.037). Also, admission sTM predicts need for RBC (ROC AUC 0.605 (0.517-0.693), p=0.018), FFP (ROC AUC 0.582 (0.495-0.669), p=0.067) and platelets (ROC AUC 0.614 (0.523-0.705), p=0.016) during ICU stay.

Renal Replacement Therapy (RRT) (Single Organ Failure)

Admission sTM predicts the 90-day need for dialysis therapy by ROC with AUC 0.688 (0.595-0.782), p<0.001.

Together, these findings indicate that early and continued measurement of blood or plasma thrombomodulin levels in patients with sepsis, severe sepsis, or septic shock will allow identification of high-risk patients i.e., patients with systemic endothelial damage and thus patients with the highest thrombomodulin levels or highest increases in thrombomodulin. High-risk patients with high thrombomodulin levels due to systemic endothelial damage will benefit from therapy with low-dose prostacyclin or analogs thereof, which will be safe in sepsis, severe sepsis, or septic shock patients due to the low-dose regimen.

Disease severity scores for sepsis were: Simplified Acute Physiology Score II (SAPS II) [evaluated at admission], and Sequential Organ Failure Assessment (SOFA) score [evaluated daily in the ICU] [sepsis].

Together, these findings indicate that early and continued measurement of blood or plasma thrombomodulin levels in patients with sepsis/severe sepsis/septic shock will allow identification of high-risk patients i.e., patients with systemic endothelial damage and thus patients with the highest thrombomodulin levels or highest increases in thrombomodulin. High-risk patients with high thrombomodulin levels due to systemic endothelial damage will benefit from therapy with low-dose prostacyclin or analogs thereof, which will be safe in these patients due to the low-dose regimen.

Example 12—Rapid Method of Identifying Patients with Systemic Endotheliopathic Syndrome The inventors have discovered a new disease entity, systemic endotheliopathic syndrome. Patients with systemic endotheliopathic syndrome suffer from acute critical illness and concurrent evidence of systemic endothelial cell damage identified by increases in circulating levels of a specific marker reflecting endothelial cell damage. Consequently, identification of patients with systemic endotheliopathic syndrome among acute critically ill patients can be done by measuring circulating levels of thrombomodulin, a specific marker of endothelial cell damage with a high sensitivity for diagnosing systemic endotheliopathic syndrome. The fact that patients with systemic endotheliopathic syndrome can be identified by a pre-determined threshold level of circulating thrombomodulin introduces personalized medicine into the invention, which is opposite to the "one size fits all" strategy currently used in medical care. Personalized medicine refers to therapy fitted to the individual patient based on risk stratification, disease phenotype, genetic profile etc.

Accordingly, acute critically ill patients with systemic endotheliopathic syndrome can be rapidly identified (and diagnosed as having that syndrome) using a method that involves measuring thrombomodulin level in a biological sample of the acute critically ill patient, and comparing the measured thrombomodulin level to a predetermined threshold.

Preferably, the thrombomodulin test is a quick point-of-care (POC) test based on whole blood input so a drop of whole blood is placed onto e.g. a lateral flow assay (stick) or another immunoassay platform like e.g. cartridges based on microfluidics technology, to display a result within 2-5 minutes reporting whether a patient has a thrombomodulin level above or below a predetermined threshold level.

It is suggested that thrombomodulin may be detected using a quick POC test such as lateral flow assays (sticks) or other immunoassay platforms like e.g. cartridges based on microfluidics technology, as the time to receive a result would significantly decrease, e.g. assays could be performed en route aboard an ambulance between a site of an accident and a trauma center or immediately upon hospital admission/recognition of acute critical illness. Obtaining a result from a POC test within minutes (instead of hours) would allow rapid allocation to prostacyclin therapy for patients with systemic endotheliopathic syndrome.

As a proof of concept, that soluble thrombomodulin in whole blood is a sufficiently sensitive marker over plasma, the present inventors performed a measurement of soluble thrombomodulin by ELISA in whole blood versus plasma.

Measurement of Soluble Thrombomodulin by ELISA in Whole Blood Compared to Plasma Background In the enzyme linked immunosorbent assay (ELISA) method, bound antigen (or antibody) is detected by an antibody linked (primarily or secondarily) to an enzyme whose activity can be determined. The activity of the antibody-linked enzyme serves as a quantitative estimate of the amount of the investigated antigen (or antibody) in the biological specimen.

In thrombomodulin ELISA, patient sample (typically plasma or serum) is added to ELISA wells pre-coated with an antibody directed against thrombomodulin. After a washing step, a detection antibody directed against (another epitope on) thrombomodulin is added (the detection antibody may be primarily or secondarily linked to an enzyme whose activity can be determined). The amount of enzyme activity in each sample is mathematically converted to a concentration measure based on the enzyme activity in samples with known amounts of thrombomodulin (standard curve).

When the thrombomodulin level in acute critically ill patients is used to guide therapy it is pivotal that the thrombomodulin test can be performed rapid. One way to speed up testing is to measure thrombomodulin in whole blood instead of plasma/serum as whole blood requires no blood sample processing (it takes ~15-20 min to prepare plasma and ~30-60 min to prepare serum from a whole blood sample).

Since not all molecules can be easily detected in whole blood (whole blood may contain substances that can interfere with specificity of the test), the inventors investigated if thrombomodulin was directly detectable in whole blood when measured by ELISA. By conducting the below described experiments, the inventors surprisingly discovered that thrombomodulin could be precisely and accurately detected in whole blood.

Experiments

Whole blood from 10 healthy human volunteers was sampled (two tubes 4 ml EDTA tubes from each subject). From each person, one tube was spun at 3000 rpm for 10 min to generate plasma and one tube was left unprocessed (whole blood). Immediately after the spinning (plasma), plasma and whole blood was pipetted onto the ELISA plate.

From each subject, the following duplicates of plasma/whole blood was investigated for its thrombomodulin content:

I) Plasma diluted 1:2 with assay buffer (golden standard and recommended for the ELISA)
II) Whole blood undiluted
III) Whole blood diluted 1:2 with assay buffer
IV) Whole blood diluted 1:4 with assay buffer Besides using whole blood as sample material, the ELISA was conducted according to the manufacturer's recommendations.

The hematocrit values from the healthy volunteers was calculated from an expected normal hemoglobin concentration of 8.3-10.5 mmol/l in male (mean 9.4 mmol/l) and 7.3-9.5 mmol/l in female (mean 8.4 mmol/l) corresponding to hematocrit values of 42% in female and 48% in male volunteers (meaning that the plasma content in whole blood was 58% in female and 52% in male).

Results

Table 8 displays the measured thrombomodulin levels in 1:2 diluted plasma (golden standard) and in different dilutions of whole blood.

In plasma, the mean thrombomodulin concentration was 1.92 (SD 0.12) ng/ml in the 10 healthy volunteers, with a low intra-assay variation between duplicates (CV %, corresponding to high precision) of 6.9%.

In undiluted whole blood, the mean concentration was 0.78 (SD 0.06) ng/ml and after correcting for hematocrit (hct) it was 1.38 (SD 0.30) ng/ml, corresponding to a recovery of 71.5% (SD 5.9%) compared to plasma. Notably, the precision of the test in undiluted whole blood was extremely high with mean CV % between duplicates only being 8.8% (Table 8). Also, the linear correlation between plasma and undiluted whole blood levels of thrombomodulin revealed a strong Pearson product moment correlation, r=0.93, yielding a high coefficient of determination, $r^2$=0.87 (FIG. 9a) (meaning that 87% of the variation in one variable was statistically explained by variation in the other variable, i.e. an extremely good fit). The thrombomodulin concentration in plasma and undiluted whole blood was significantly different (p=0.002, paired t-test) with the correction-factor being (1-71.5)/71.5=1.4, emphasizing that thrombomodulin could be measured precisely in undiluted whole blood.

In 1:2 diluted whole blood, the mean concentration was 1.23 (SD 0.33) ng/ml and after correcting for hematocrit (hct) it was 2.16 (SD 0.59) ng/ml, corresponding to a recovery of 110.9% (SD 15.8%) compared to plasma. The precision of the test in 1:2 diluted whole blood was extremely high with mean CV % between duplicates only being 10.3% (Table 8). The linear correlation between plasma and undiluted whole blood levels of thrombomodulin revealed a strong Pearson product moment correlation, r=0.91, yielding a high coefficient of determination, $r^2$=0.83 (FIG. 9b) (meaning that 83% of the variation in one variable was statistically explained by variation in the other variable, i.e. an extremely good fit). The thrombomodulin concentration in plasma and undiluted whole blood was comparable (not different, p=0.296, paired t-test), emphasizing that thrombomodulin could be measured precisely and accurately in whole blood diluted 1:2.

In 1:4 diluted whole blood, the mean concentration was 1.04 (SD 0.51) ng/ml and after correcting for hematocrit (hct) it was 1.83 (SD 0.90) ng/ml, corresponding to a recovery of 90.19% (SD 33.4%) compared to plasma. The precision of the test in 1:4 diluted whole blood was acceptable with mean CV % between duplicates being 21.0% (Table 8). The linear correlation between plasma and undiluted whole blood levels of thrombomodulin revealed a strong Pearson product moment correlation, r=0.93, yielding a high coefficient of determination, $r^2$=0.86 (FIG. 9c) (meaning that 86% of the variation in one variable was statistically explained by variation in the other variable, i.e. an extremely good fit). The thrombomodulin concentration in plasma and undiluted whole blood was comparable (not different, p=0.762, paired t-test), emphasizing that thrombomodulin could be measured accurately in whole blood diluted 1:4.

Conclusion

This experiment demonstrated that thrombomodulin was easily detectable in whole blood. This emphasizes that thrombomodulin has biochemical features that allows thrombomodulin antibodies to detect this molecule also in whole blood i.e., a significantly more complex biological sample matrix than plasma. The precision of the thrombomodulin measurement in undiluted whole blood was extremely high and 1:2 dilution of the whole blood retained precision and improved accuracy.

Based on the results of this experiment, the inventors infer that thrombomodulin can be easily measured in a whole blood based quick assay like e.g. a dipstick. This may allow rapid treatment stratification of acute critically ill patients when this is based on their thrombomodulin levels.

Qualified Diagnosis of Systemic Endotheliopathy by Adding Measurement of Other Biomarkers I.E. Syndecan-1, Adrenaline and Vascular Endothelial Growth Factor (VEGF) in Some Patients The diagnosis of systemic endothelial damage i.e. systemic endotheliopathic syndrome (SES) in acute critically ill patients may in some patients be further qualified besides that obtained by measuring thrombomodulin levels pre-hospital or at hospital admission/recognition of acute critical illness. Thus, adding a pre-hospital or at hospital admission measurement of syndecan-1 (a biomarker reflecting endothelial glycocalyx damage) and/or adrenaline (a endogenous stress biomarker directly drivers endothelial damage) will aid the diagnosis of "systemic endotheliopathic syndrome".

Patients, in particular trauma patients, with thrombomodulin levels just above a given cut-off but with concurrent syndecan-1 and adrenaline levels above their given cut-offs, suffer from severe systemic endotheliopathic syndrome. These patients, with borderline increased thrombomodulin but high syndecan-1 and adrenaline levels, are thus at higher-than-expected (based on thrombomodulin) risk of disease progression and organ failure and excess mortality, and these patients will benefit from prostacyclin therapy as described above. The prostacyclin therapy should be initiated earliest possible and monitored daily by thrombomodulin and clinical disease scores, as described above.

Thus, similar to thrombomodulin, the measurement of syndecan-1 and adrenaline as additional biomarkers that can diagnose and qualify the severity of systemic endotheliopathy i.e. systemic endotheliopathic syndrome. Preferably, all biomarkers (thrombomodulin, syndecan-1, adrenaline) are measured either individually or simultaneously by a quick POC assay either pre-hospital or immediately upon hospital admission/recognition of the acute critical illness. Applying a quick POC assay that reveal results within a few minutes, enables fast diagnosis of systemic endotheliopathic syndrome and hereby a fast risk stratification and initiation of prostacyclin therapy. Prompt initiation of prostacyclin therapy will minimize further progression of the endotheliopathy in the early phase of the acute critical illness and will thus enable fast reversal and treatment of the endotheliopathy.

Evidence from Trauma

In 635 trauma patients, high syndecan-1 and adrenaline levels were strong and independent predictors of mortality.

FIG. 10 shows a receiver operating characteristic (ROC)-curve of syndecan-1 for predicting mortality in trauma patients. Syndecan-1 AUC for predicting 28-day mortality: AUC 0.599 (0.537-0.661), p=0.001. Highest Youden Index reveals a threshold level of 40 ng/ml syndecan-1 in plasma. Sensitivity 0.569, 1-specificity 0.354.

FIG. 11 shows a receiver operating characteristic (ROC)-curve of Adrenaline for predicting mortality in trauma patients. Adrenaline AUC for predicting 28-day mortality: AUC 0.629 (0.567-0.691), p<0.0001. Highest Youden Index reveals a threshold level of 225 pg/ml Adrenaline in plasma. Sensitivity 0.658, 1-specificity 0.435.

When using the above cut-offs for syndecan-1 (40 ng/ml) and adrenaline (225 pg/ml), the following hazards ratios (HR) for 28-day mortality were revealed:
Plasma syndecan-1 above 40 ng/ml: HR 2.16 (95% CI 1.43-3.24), Wald 14, p<0.0001
Plasma adrenaline above 225 pg/ml: HR 2.47 (95% CI 1.61-3.80), Wald=17, p<0.0001

The power of these cut-off can be illustrated by the proportion of patients dying within 1-28 days when stratified according to syndecan-1 or adrenaline level ad admission.

1-Day Mortality:

Patients with syndecan-1 levels>40 ng/ml at admission have a 4-fold higher <24 h mortality compared to patients with syndecan-1 levels<40 ng/ml (10.4% vs. 2.7%, p<0.0001). Patients with adrenaline levels>225 pg/ml have 4-fold higher <24 h mortality compared to patients with adrenaline levels<225 pg/ml (8.5% vs. 2.1%, p<0.0001).

Especially for early mortality (<24 h) risk, adding syndecan-1 and adrenaline measurements and their cut-off levels to that of thrombomodulin, tends to improve the diagnosis of traumatic endotheliopathy and thus risk stratification allowing early treatment initiation (syndecan-1 adding significant value compared to thrombomodulin: p=0.153 and adrenaline adding significant value compared to thrombomodulin: p=0.085). The strength for early mortality prediction emphasizes the need for fast diagnosis of systemic endotheliopathic syndrome by POC assays allowing a fast initiation of prostacyclin therapy.

28-Day Mortality:

Patients with syndecan-1 levels>40 ng/ml at admission have a 2-fold higher 28-day mortality compared to patients with syndecan-1 levels<40 ng/ml (26% vs. 14%, p<0.0001). Patients with adrenaline levels>225 pg/ml have more than 2-fold higher 28-day mortality compared to patients with adrenaline levels<225 pg/ml (25% vs. 11%, p<0.0001)

When applying other cut-offs than 40 ng/ml for syndecan-1 and 225 pg/ml for adrenaline, the sensitivities and 1-specificities are obtained (data from 635 trauma patients), as shown in Table 9 and 10, respectively.

Finally, in addition to thrombomodulin and/or syndecan-1 and/or adrenaline, measurements of the vascular endothelial growth factor (VEGF) level in patients suffering from acute critical illness can diagnose patients with systemic endotheliopathic syndrome whom have excessive loss of vascular integrity i.e., excessive loss of fluids out of the intra vascular compartment. Risk stratification and prostacyclin therapy based on cut-off levels of VEGF measured pre-hospital or at admission/recognition of acute critical illness represents yet another tool to personalize care for acute critically ill patients.

Thus, a patient is considered to have systemic endotheliopathic syndrome (also denoted systemic endotheliopathy or simply endotheliopathy) when the patient suffers from acute critical illness AND is diagnosed with systemic endothelial damage.

The invention claimed is:

1. A method of diagnosing for an individual diagnosed with an acute critical illness, if said individual is a candidate for combination treatment of standard care for said acute critical illness in combination with administration of prostacyclin or an analogue thereof, wherein said acute critical illness is selected from trauma, burn injury trauma, sepsis, severe sepsis, septic shock, acute myocardial infarction, cardiac arrest, systemic inflammatory response syndrome (SIRS), acute major surgery, shock, or a thromboembolic event, said method comprising:
    measuring a baseline concentration of soluble thrombomodulin in blood or plasma of said individual;
    determining if said baseline concentration of soluble thrombomodulin in blood or plasma is above a threshold level of at least 2.5 ng/ml; and
    administering the combination treatment of standard care for said acute critical illness in combination with administration of prostacyclin or an analogue thereof to said individual period if said baseline concentration of soluble thrombomodulin in blood or plasma is above said threshold level of at least 2.5 ng/ml.

2. A method according to claim 1 wherein said threshold level is at least 4ng/ml.

3. A method according to claim 1 wherein said method is a method of diagnosing severe endothelial damage in said individual diagnosed with said acute critical illness; wherein said individual is diagnosed with severe endothelial damage in addition to said acute critical illness, if said baseline concentration is above said threshold level.

4. A method according to any of the claims 1, wherein said method is a method of diagnosing systemic endotheliopathic syndrome in an individual diagnosed with an acute critical illness; wherein said individual is diagnosed with systemic endotheliopathic syndrome when said individual is diagnosed with both an acute critical illness and severe endothelial damage.

5. A method of using thrombomodulin as a biological marker in diagnosing for an individual diagnosed with an acute critical illness, if said individual is a candidate for combination treatment with standard care for said acute critical illness in combination with administration of prostacyclin or an analogue thereof, wherein said acute critical illness is selected from trauma, burn injury trauma, sepsis, severe sepsis, septic shock, acute myocardial infarction, cardiac arrest, systemic inflammatory response syndrome (SIRS), acute major surgery, shock, or a thromboembolic event, said method comprising:
    measuring a baseline concentration of soluble thrombomodulin in blood or plasma of said individual;
    determining if said baseline concentration of soluble thrombomodulin in blood or plasma is above a threshold level of at least 2.5 ng/ml; and
    administering the combination treatment of standard care for said acute critical illness in combination with administration of prostacyclin or an analogue thereof to said individual if said baseline concentration of soluble thrombomodulin in blood or plasma is above said threshold level of at least 2.5 ng/ml.

6. A method according to claim 5 wherein said threshold level is at least 4 ng/ml.

7. A method according to claim 5, wherein said method is a method of diagnosing severe endothelial damage in said individual diagnosed with said acute critical illness; wherein said individual is diagnosed with severe endothelial damage in addition to said acute critical illness, if said baseline concentration is above said threshold level.

8. A method according to claim 5, wherein said method is a method of diagnosing systemic endotheliopathic syndrome in an individual diagnosed with an acute critical illness; wherein said individual is diagnosed with systemic endotheliopathic syndrome when said individual is diagnosed with both an acute critical illness and severe endothelial damage.

9. A method of treating an acute critical illness in an individual diagnosed with said acute critical illness and concurrent increase in a measured thrombomodulin level in blood or plasma of said individual, wherein said acute critical illness is selected from trauma, burn injury trauma, sepsis, severe sepsis, septic shock, acute myocardial infarction, cardiac arrest, systemic inflammatory response syndrome (SIRS), acute major surgery, shock, or a thromboembolic event, said method comprising:
    (a) measuring a baseline concentration of soluble thrombomodulin in blood or plasma of said individual;
    (b) determining if said baseline concentration of soluble thrombomodulin in blood or plasma is above a threshold level of at least 2.5 ng/ml;
    (c) administering a dose of 0.5 - 4 ng/kg/min of prostacyclin or an analogue thereof to said individual continuously for a first time period if said baseline concentration of soluble thrombomodulin in blood or plasma is above said threshold level of at least 2.5 ng/ml;
    (d) measuring at the end of said first time period a concentration of soluble thrombomodulin in blood or plasma of said individual;
    (e) determining if said concentration of soluble thrombomodulin is lower by at least a decrease of 10% compared to said baseline concentration of thrombomodulin determined prior to initiation of said prostacyclin administration;
    (f) assessing if a clinical improvement of said acute critical illness in said individual has occurred during said first time period; and
    (g) if both a concentration reduction and a clinical improvement is observed, ceasing prostacyclin administration while continuing standard care for said acute critical illness; or
    (h) otherwise continue prostacyclin administration for a second time period not exceeding said first time period wherein the steps (d) to (h) are repeated until ceasing prostacyclin administration to said individual following step (g).

10. A method according to claim 9, wherein said threshold level is at least 4ng/ml.

11. A method according to claim 9 wherein said dose is 1 - 2ng/kg/min.

12. A method according to claim 9, wherein said analogue of prostacyclin is either Iloprost or Flolan.

13. A method according to claim 9, wherein said first time period is at least 48 hours or at least 72 hours.

14. A method according to claim 9, wherein said second time period is 12 hours or 24 hours.

15. A method according to claim 9, wherein in step (e) said decrease is at least 20%.

16. A method according to claim 9, wherein said baseline concentration is measured immediately after or shortly after recognition of said acute critical illness.

17. A method according to claim 9, wherein said prostacyclin administration is initiated immediately or shortly after a completion of step (b) has determined that said baseline concentration of soluble thrombomodulin in blood or plasma is above said threshold level.

18. A method according to claim 9, wherein prostacyclin or an analog thereof is administered as according to step (c) prior to steps (a) and (b) having been completed.

19. A method according to claim 9, wherein said concurrent increase in a measured thrombomodulin level in blood or plasma of said individual is the result of severe endothelial damage.

20. A method according 1, wherein the measurement of thrombomodulin, is conducted by a point-of-care (POC) assay.

21. A method according to claim 9 wherein the measurement of thrombomodulin, is conducted by a point-of-care (POC) assay.

* * * * *